United States Patent [19]

Park

[11] Patent Number: 4,589,782
[45] Date of Patent: May 20, 1986

[54] THERMOCENTRIFUGOMETRIC ANALYSIS

[75] Inventor: Jin Y. Park, Moscow, Id.

[73] Assignee: Research Corporation, N.Y.

[21] Appl. No.: 618,961

[22] Filed: Jun. 11, 1984

Related U.S. Application Data

[63] Continuation-in-part of Ser. No. 504,233, Jun. 14, 1983, abandoned.

[51] Int. Cl.⁴ ............................................. G01N 25/00
[52] U.S. Cl. ................................... 374/14; 73/432 R
[58] Field of Search ......................... 73/432 R, 432 G; 374/14

[56] References Cited

U.S. PATENT DOCUMENTS

| | | |
|---|---|---|
| Re. 26,100 | 10/1966 | Cahn . |
| 2,515,056 | 7/1950 | Petit . |
| 2,609,617 | 9/1952 | Hall . |
| 2,814,944 | 12/1957 | Brown . |
| 2,826,079 | 3/1958 | Kuder et al. . |
| 2,882,717 | 4/1959 | Brown . |
| 2,907,117 | 10/1959 | Parkinson et al. . |
| 3,167,143 | 1/1965 | Savage . |
| 3,194,332 | 7/1965 | Wiedemann . |
| 3,292,417 | 12/1966 | Haydon et al. ........................ 374/14 |
| 3,717,210 | 2/1973 | Sieswerda . |
| 3,812,924 | 5/1974 | Fletcher et al. . |
| 3,813,928 | 6/1974 | Anderson . |
| 3,902,354 | 9/1975 | Harlan et al. ......................... 374/14 |
| 3,973,636 | 8/1976 | Uchida . |

OTHER PUBLICATIONS

C. J. Keattch, FRIC, An Introduction to Thermogravimetry, Heyden & Sons Ltd. et al, 1969 pp. 8–10.

J. M. Smith, Chemical Engineering Kinetics, 1981, McGraw-Hill, pp. 535–537, 640–642.
O. Levenspiel, John Wiley & Sons, Inc., Chemical Reaction Engineering, 1972 pp. 485–487.

Primary Examiner—Stewart J. Levy
Assistant Examiner—Tom Noland
Attorney, Agent, or Firm—Scully, Scott, Murphy & Presser

[57] ABSTRACT

A method and six devices for measuring the change in mass of a sample subjected to selected temperatures and fluid variables is disclosed. The test sample is subjected to centrifugal force to amplify the "apparent mass" of the sample by rotating the sample about a first axis of rotation. Any change in the mass of the test sample is then amplified by the centrifugal force and measured by the displacement or the displacement force of the sample. The above method and six separate devices are disclosed. The first device balances the mass of the test sample against a known reference weight. The second device generates a counter-rotational force about a second axis to bring the sample to a "nulled" position. The third device balances the force generated about the second axis against a known and adjustable balance beam. A reciprocating means is used to couple the balance beam to a rotating sample holder. The fourth device generates a counter force along the balance beam to bring the sample to a "nulled" position. The radial displacement force is measured in the fifth device and the radial displacement is measured in the sixth device. The devices are particularly adapted for mass change analysis in high temperature environments using high sweep gas rates and a variety of gaseous fluids.

75 Claims, 25 Drawing Figures

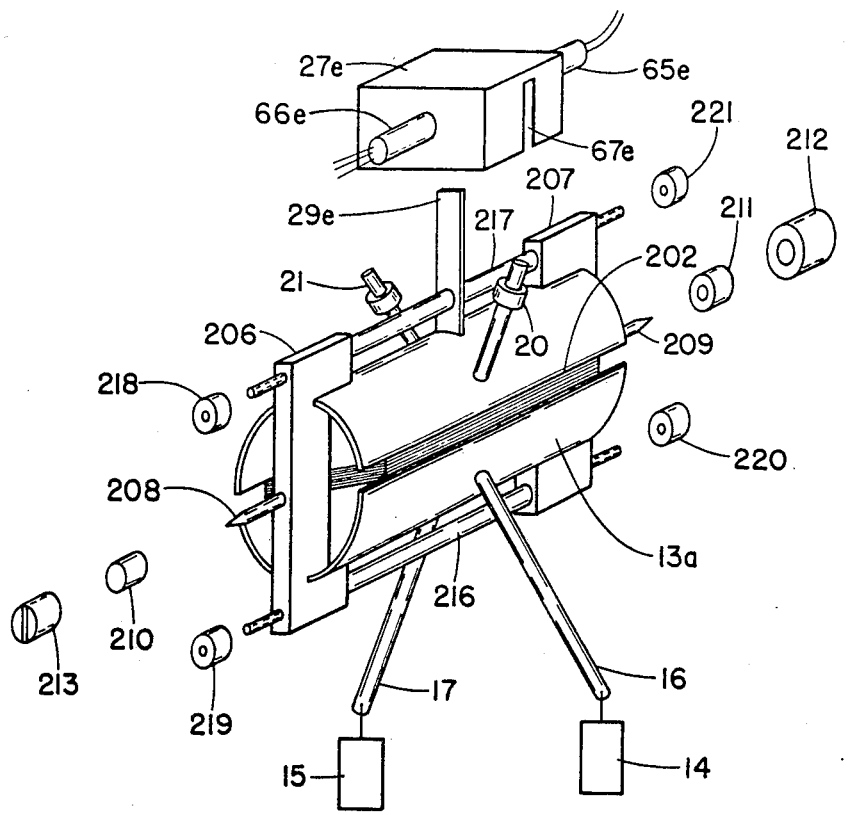
FIG.4
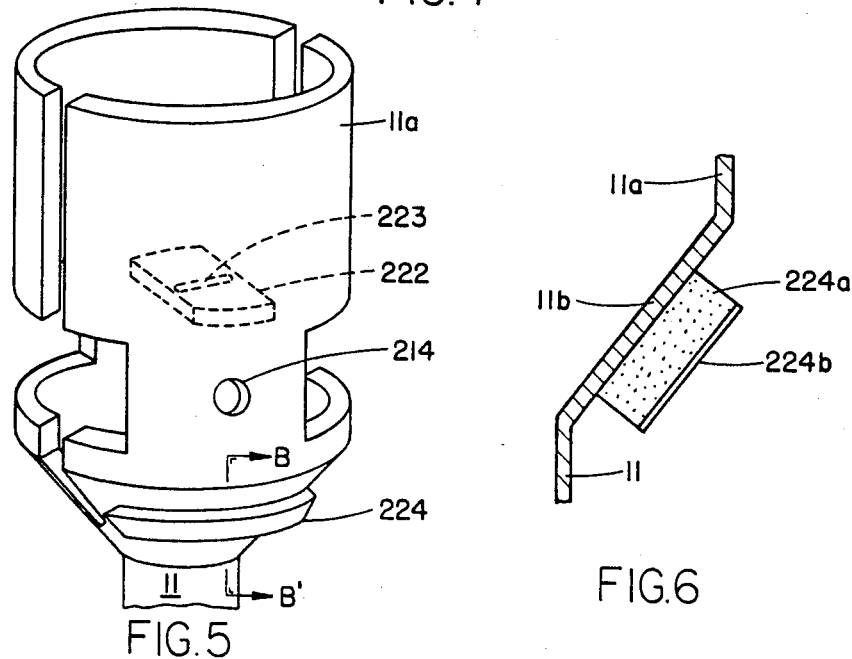
FIG.5
FIG.6

$$\frac{(\text{CONTAINER LENGTH})}{(\text{CIRCULATION VELOCITY})} \Big/ \text{PERCOLATION VELOCITY}$$

THERMOCENTRIFUGOMETRIC ANALYSIS

CROSS REFERENCE TO RELATED APPLICATIONS

This application is a Continuation-In-Part of U.S. Ser. No. 504,233 filed June 14, 1983, entitled Thermocentrifugometric Analysis, the disclosure of which is incorporated herein by reference thereto, now abandoned, but which is continued in the daughter application Ser. No. 686,341 filed Dec. 26, 1984 as a continuation application thereof.

BACKGROUND OF THE INVENTION

1. Field of the Invention

The present invention relates to a scientific instrument capable of performing conventional thermogravimetric analysis. The instrument is also capable of measuring the mass of an unknown sample in ambient atmosphere. Further, the invention provides a heretofore unknown method of measuring the continuous mass change of a solid subjected to high sweep gas velocities. Further, the invention will perform continuous mass change analysis with both high sweep gas velocities and elevated temperatures.

Conventional thermogravimetric analysis techniques are subject to fluctuating and unstable weight readings as the sweep gas flow past the solid being analyzed is increased. The fluctuations not only reduce the accuracy of measurement at low gas flow rates, but may also grow very rapidly, totally invalidating thermogravimetric analysis weight readings even at moderate sweep gas flow rates. J. M. Forgac and J. C. Angus, in "A Pressurized Thermobalance Apparatus For Use at Extreme Conditions," (Industrial and Engineering Chemistry Fundamentals, Volume 18, No. 4, Page 416 (1979)) reported that the weight reading became unstable due to a natural convection current induced by the temperature difference between the gas and the solid.

This instability severely limits the application of thermogravimetric analysis techniques in the kinetic study of fast gas-solid reactions at elevated pressures and temperatures because:

(a) a high sweep gas rate, required to enhance the contact between gas and solid and thereby determine the reaction kinetics (exclusive of external heat and mass transfer resistances) generates intense flow turbulences which cause instability of the weight measurement;

(b) the flow turbulence generated increases as the gas is compressed to elevated pressures. The compressed gas then exerts an increased impact on the suspended solid;

(c) the temperature gradient developed about the solid generates a free convection current which adds to the flow turbulence.

The stability problems originate from the simple fact that gravity is a very weak force field and is easily disturbed by flow turbulences. It is generally considered unavoidable in conventional thermogravimetric analysis techniques. Due to the stability limitation of the conventional gravimetric mass measurement, the sweep gas velocity in conventional thermogravimetric reactors is very restricted and is seldom allowed to exceed 0.1 m/s. In this range of sweep gas velocity, the gas-solid mass and heat transfer rates are very low, $Nu=2$ as predicted by the Froessling equation, and the reaction often proceeds in the presence of significant temperature and composition gradients. The limitation on the sweep gas velocity is most pronounced at high pressures (high gas densities) and high temperatures (thermal disturbances) typical of industrial gas-solid reaction conditions.

The field of use for the present invention includes not only its application as a scientific instrument in the measurement of mass, but also in the duplication of measurements obtained in conventional thermogravimetric analysis. It also makes possible the measurement of the mass change of a solid subjected to high sweep gas velocities at elevated temperatures and pressures. Many industrially important gas-solid reactions are conducted at elevated pressures and temperatures such as those in coal gasification, coal combustion, oil shale retorting, dolomite sulfation, biomass pyrolysis, and mineral conversions.

Thermogravimetric analysis has rarely been used for liquid-solid contact systems because of the instability problems. The strong centrifugal force field of the present invention however makes possible the measurement of the mass and its change of a solid immersed in liquid. The present invention therefore also provides useful experimental means for the kinetic study of liquid-solid reactions such as those in coal liquification, leaching of minerals and ores, and purification of polluted water by activated carbon.

2. Discussion of the Prior Art

A conventional thermogravimetric analysis is disclosed in U.S. Pat. No. 3,973,636 which issued to Hiroshi Uchida on Aug. 10, 1976. This device is essentially a balance beam having a known reference material applied to one end of the balance beam and a test sample applied to the other end. The known reference material and the test sample are then subjected to high temperatures while any change in mass of the test sample is detected by an electromagnetic pickup device.

A general summary of thermogravimetric techniques may be found in "An Introduction to Thermogravimetry" by C. J. Keattch, FRIC published by Heyden and Son, Ltd. in cooperation with Sadtler Research Laboratories Inc., Page 1-14, 1969).

U.S. Pat. No. 3,812,924 to Fletcher et al. on May 28, 1974 discloses a device for monitoring a change in mass in varying environments. This device is a cantilever beam device using a strain gauge as the transducer for reflecting the change in mass of the sample.

The foregoing patents and the book excerpt describe conventional systems for thermogravimetric mass analysis. As discussed above, conventional systems are not capable of measuring the continuous mass change of a test solid under high sweep gas velocities.

The two most widely used laboratory reactors for fluid-solid reaction studies are described on pages 535 to 537 of the textbook entitled "Chemical Engineering Kinetics" 3rd Edition, authored by J. M. Smith, published by McGraw Hill Book Company in 1981. These reactors provide uniform fluid conditions and high fluid-solid contacting velocities. However, they are not capable of measuring the changing mass of the reacting solid. This textbook does describe on Page 640–642 a prior attempt to obtain uniform fluid conditions at high fluid-solid contacting velocities in conventional thermogravimetric analysis. This technique has had some success with an extremely big and heavy single suspended particle with a diameter greater than one inch. It is not capable of handling ordinary solid particles which are much smaller than one inch. The device illustrated, on page 641 (FIG. 14-2) is a stirred-tank single-pellet reactor used for the kinetic study of hydrofluorination of uranium dioxide.

Basket-type mixed reactors are also used in gas-solid contact systems. Such a device is disclosed in pages 485–487 of "Chemical Reaction Engineering", 2nd Edition by Octave Levenspiel, published by John Wiley and Sons, Inc. in 1972.

The fluid-solid contact devices disclosed above are not capable of measuring continuous mass changes in test samples under high sweep gas rate velocities. Even in the "stirred-tank single pellet reactor" the stirring speed is very restricted due to the stability limitation.

The present invention uses centrifugal force to amplify the weight of the sample to be tested. In conventional thermogravimetric analysis, the weight of the sample is determined by the gravitational pull on the mass of the sample. In the present invention, the weight of the sample is greatly amplified by centrifugal force.

U.S. Pat. No. 2,826,079 which issued to M. L. Kuder et al. on Mar. 11, 1958 discloses an automatic coin weighing machine which in FIG. 5 discloses a standard reference weight indicated by the numeral 4, and a coin to be sampled indicated by the numeral 5. If the coin is a counterfeit coin the difference in weight between the standard reference weight and the counterfeit coin will displace the center of mass slightly from the geometric center of the wheel. The apparatus then detects the displacement with an electronic mutual inductance micrometer. This patent teaches the concept of magnifying the apparent mass of the sample to be tested by nearly 500 times. This magnifies the small weight differential between the standard reference weight and the counterfeit coin 500 fold.

U.S. Pat. No. 2,814,944 to R. E. Brown issued on Dec. 3, 1957 discloses a centrifugal testing apparatus for instruments. This device has some structural similarities to the structures employed in one of the embodiments of applicant's invention. In this device, a pair of outwardly extending support arms rotate about a center axis. Each of the outwardly extending support arms carries a basket. One of the baskets is loaded with the instruments to be tested, the other basket is loaded with the appropriate counterweights to balance out the centrifuge. Dynamic unbalance above a predetermined tolerance is detected automatically and corrected by a servo-motor within the mechanism. If the dynamic imbalance is too high, the mechanism is shut down completely.

It should be noted that neither of the devices illustrated in the Brown '944 patent nor the Kuter et al. '079 patent are capable of measuring a mass change in a coin or in the instrument. In addition, they are not capable of measuring a mass change under extreme thermal conditions, or under high sweep gas velocities and elevated temperatures and pressures.

SUMMARY OF THE INVENTION

The present invention discloses a process and several devices for measuring the change in mass of a test sample subjected to selected temperatures and fluid variables. The process includes the step of balancing the test sample against a known reactive force while the sample is suspended in an angularly displaceable sample receiving means. For each of the devices, the reactive force may be a known reference weight, or a null device which restores the angular rotation of the sample to a given null point. The sample receiving means is rotated about a first axis to amplify the apparent mass of the sample by centrifugal force. The speed of rotation may be held constant or may be varied. Changes in the speed of rotation may be used to dynamically balance the rotating mass, or to rebalance the rotating mass after a change in mass. When the desired apparent amplification of the mass has been achieved, the test sample may be subjected to selective temperature and fluid variables. The invention then measures the change in angular or radial displacement, or in the angular or radial displacement force generated by the test sample as it is subjected to the centrifugal force and the selected temperature and fluid variables. The change in mass of the test sample may then be measured by a derivative value of the change in displacement force, or a change in its angular or radial displacement.

In one embodiment of the invention, the thermocentrifugometric mass analyzer includes a rotating shaft and two rotor arms for balancing a test sample against a standard reference material. After compensating for gravimetric balance between the sample and the reference material, the two rotor arms are rotated at high speed while the test sample is subjected to thermal analysis, or fluid-solid interchange. As the two rotor arms rotate, any imbalance in the mass in the test sample over the mass in the standard reference will cause the rotor disc to be angularly displaced. This displacement is a function of the difference in mass between the known standard and the mass of the test sample undergoing analysis. The angular displacement may be measured and calibrated through a variety of techniques.

In a second embodiment of the thermocentrifugometric analyzer, the angular displacement of the rotor is opposed by a null motor apparatus which senses the angular displacement of the rotor and generates a counter-reactive force to restore it to its original position. The amount of reactive force necessary to maintain the rotor at the null point is then used to measure the mass of the test sample. In addition, the null point apparatus may be combined with a variable speed motor to rebalance the device to achieve dynamic balance, or to rebalance the device after a change in mass. The mass measurement may then be derived from the amount of reactive force, the speed of rotation or a combination of both.

In a third embodiment of the present invention one or more rotor arms are provided which are biased against a balance beam positioned over a reciprocating rod connected to the rotor arm. Means are provided for calibrating the balance beam to provide a known reactive force for the sample as it is subjected to centrifugal force. After the first reference value is generated by the balance beam, any change in mass in the test sample will be measured directly by a change in the balance beam position as the test sample undergoes analysis.

A fourth embodiment of the present invention represents the null balance operation mode of the third embodiment. The vertical displacement of the reciprocating rod is opposed by a null balance device which senses the vertical displacement and generates a counter-reactive force to restore it to its original position. The amount of reactive force to maintain the piston at the null point is then used to measure the mass of the tested sample.

Both the third and forth embodiments may be combined with a variable speed motor to rebalance the device to achieve dynamic balance, or to rebalance the device after a change in mass. The mass measurement may then be derived from the known reactive force, the null balance force, the speed of rotation, or a combination of these forces.

In a fifth embodiment of the present invention, several versions of the invention are used to establish a radial displacement or a radial displacement force indicative of the mass of the test sample or the change in mass of the test sample. In addition, each of the radical displacement devices may be combined with a variable speed motor to provide an ability to dynamically balance the device, or to compensate for a change in mass. In the latter instance, a derivative value of the change in the speed of rotation can be used to indicate the change in mass.

The present invention provides a thermocentrifugometric analysis as opposed to the previously known thermogravimetric analysis. The thermocentrifugometric analysis rotates the solid at high speeds, in which the high-speed rotation not only provides very efficient interchange between the gas and solid, but also generates a very strong and stable centrifugal force field under which the changing mass of the rotating solid can be continuously measured. Since the centrifugal force field is several orders of magnitude greater than gravitational force, the measurement is extremely stable and not affected by gas-solid flow disturbances.

Moreover, the present invention provides for the amplification of the gravitational force field by centrifugal force. A 5 cm long arm rotating at 2000 rpm will provide a 224 fold increase in the mass change of the sample to be tested. By varying the speed of the rotation, there may be varied the amount of centrifugal force applied to the test sample. Thus the degree of amplification of the change in mass may be varied to accommodate various fluid-solid reactions.

The proposed thermocentrifugometric analyzer has potential use for a variety of gas-solid reaction studies, both catalytic and noncatalytic, over a broad range of applications from very fundamental surface reaction kinetic studies to actual rate measurements under the simulated conditions of industrial reactors. Some examples of its potential applications are: combustion and gasification studies on carbonaceous materials (carbon, coal, chars, biomass); oxidation and reduction studies on metals and ores; pyrolysis and calcination studies on decomposable solids (coal, oil shales, biomass, limestones); silicon and other solid deposition studies; and carbon deposition studies on fouling catalysts.

The remarkably stable mass measurement capability of a thermocentrifugometric analyzer could also allow its use for liquid-solid reaction studies for which the conventional thermogravimetric analysis has seldom been used due to its stability limitations. Some examples of its potential applications are: adsorption studies on porous adsorbent solids such as activated carbon, liquid leaching studies on ores, and coal liquification studies.

The present invention provides an extremely accurate mass measurement device that will reflect a change in mass at the nano-germ level of mass change.

It is therefore an object of the present invention to provide a novel method of measuring the change in mass of a test sample by rotating the sample about a first axis to subject the sample to centrifugal force to amplify any change in the "apparent mass" of the test sample.

It is another object of the present invention to provide a method and several means for detecting the change in the "apparent mass", by measuring centrifugal force generated by test sample about a first axis of rotation.

It is another object of the present invention to provide a method and several test instruments that will measure the change in mass at a high temperature and a variety of fluid conditions.

It is another object of the present invention to provide a centrifugometric mass analysis device that is capable of providing stable and continuous mass change readings when the test sample is subjected to elevated temperatures and pressures.

A further object of the present invention is to provide an instrument that will indicate continuous mass change readings when a material to be tested is subjected to elevated temperatures and pressures wherein the fluid is coacting with the solid at a high sweep fluid velocity. The high speed rotation provides a relative velocity of 40 meters per second within a pressurized and heated autoclave when a 10 cm arm is used while rotating at 4000 rpm. Furthermore, the high speed rotation may be readily utilized for the mixing of gas, which permits the operation of a thermocentrifugometric device as an integral mixed flow reactor.

The present invention also provides a mass measurement device to determine the mass of any unknown sample by comparing it to a known reference material while subjecting the test material and the reference material to a strong and adjustable centrifugal force.

The present invention also provides a mass measurement device to determine the mass of any unknown sample by comparing it to a known and adjustable force while subjecting the test material to a strong and stable centrifugal force.

BRIEF DESCRIPTION OF THE DRAWINGS

The foregoing objects and advantages of the centrifugometric mass analyzer may be more readily understood by one skilled in the art with reference being had to the following detailed description of the several preferred embodiments thereof, taken in conjunction with the accompanying drawings wherein like elements are designated by identical reference numerals throughout the several views, in which:

FIG. 4 is an exploded isometric view of a portion of the null motor device illustrated in FIG. 3.

FIG. 5 is an isometric view of another portion of the null motor embodiment illustrated in FIG. 3.

FIG. 6 is a cross-sectional view of a radiation reflector wherein the cross-section is taken along section line B—B' illustrated in FIG. 5.

DETAILED DESCRIPTION

Figure 1:
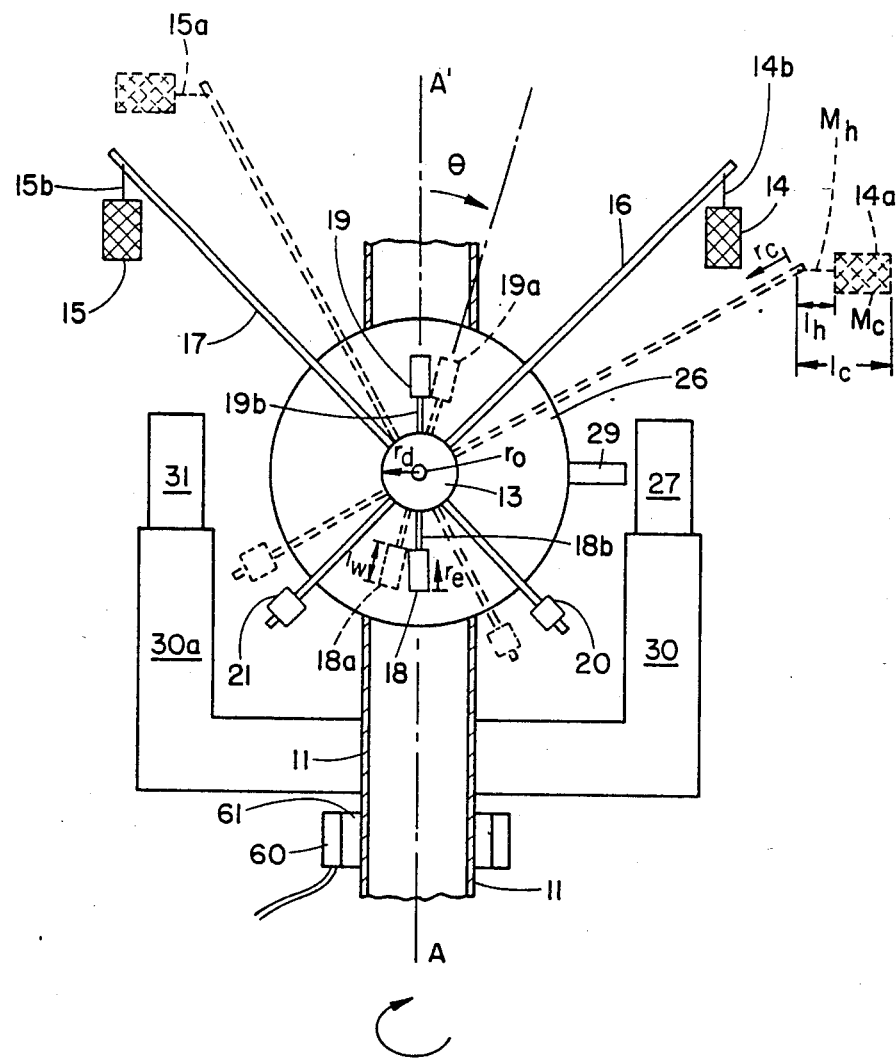
FIG. 1 is a partially cross-sectioned and front view of the angularly displaceable embodiment of the present invention illustrated in a static state through solid lines, and in a dynamic state through dotted lines.

The present invention relates to a process and several forms of mechanical apparatus for carrying out the process when it is desired to determine the change in mass of a test sample when the test sample is subjected to selected temperature and fluid variables. In conducting the process, the test sample is balanced against a known reactive force and suspended in an angularly dispaceable receiver. The known reactive force, as will be hereinafter described with respect to the several mechanical embodiments of the invention, may include a known reference weight, a null motor, a balance beam, a radial displacement arm, a variable speed motor, or one or more combinations of these.

In measuring the change in mass, the sample and its receiver are rotated about a first axis to amplify the apparent mass of the sample by centrifugal force. Thus if the initial mass of the sample were one gram, and the reference weight were one gram, the apparent mass may be amplified to 100 grams by selecting an appropriate speed of rotation, and placing the sample receiving means at an appropriate distance from the rotating axis. Both the speed of rotation, and the radius of the circle traversed by the sample may be varied to alter the apparent mass of the sample. If the apparent mass were amplified by 1000 times, a relatively small differential change in the mass of the test sample may be easily determined by measuring the angular, linear or radical displacement of the sample. In an alternate embodiment of the invention, this angular displacement about a second axis is balanced by means of a null motor. In other alternate embodiments of the invention, the angular displacement is first converted to a vertical displacement of a reciprocating piston placed along the first axis of rotation. The vertical displacement is measured in a third embodiment, and it is balanced by means of a measurable counter-reactive force in a fourth embodiment. The radial displacement force is measured in a fifth embodiment, and the radial displacement is measured in a sixth embodiment.

While the device will measure mass by comparing an unknown sample with a known reference material or force, it is particularly suited for measuring the change in mass when a test sample is subjected to one or more of the following variables:

(a) a selected temperature or series of temperatures substantially above or below the ambient atmospheric temperature;

(b) a selected atmospheric pressure or series of atmospheric pressures above or below ambient atmospheric pressure;

(c) a specific fluid-solid reaction wherein a preselected test sample is rotated in a fluid or chamber containing the reactant fluid;

(d) a selected high sweep fluid velocity or a series of high sweep fluid velocities.

The sweep fluid velocities may be altered by a plurality of means, such as the configuration of the sample container, the speed at which the sample is rotated about its first axis of rotation, the radius the circular path defined by the sample, baffling and recirculation means to agitate the gas within a test chamber, and external means for directing a high sweep gas flow into the chamber to impinge upon the rotating test sample.

The amplification of apparent mass as indicated above is dependent upon the radius of the circle defined by the test sample as it rotates, and the speed of rotation. The following table sets forth the apparent amplification of the mass at various radii of circular motion and rotational speeds.

| RPM Of Test Sample | 5 cm Arm Length | 7.5 cm Arm Length |
|---|---|---|
| 500 | 14 times $M_s$ | 21 times $M_s$ |

-continued

| RPM Of Test Sample | 5 cm Arm Length | 7.5 cm Arm Length |
|---|---|---|
| 1000 | 56 times $M_s$ | 84 times $M_s$ |
| 2000 | 224 times $M_s$ | 336 times $M_s$ |
| 4000 | 896 times $M_s$ | 1344 times $M_s$ |
| 5000 | 1400 times $M_s$ | 2100 times $M_s$ |

The arm length described above is the radius of the circle defined by the test sample.

While the amplification of mass by centrifugal force is a well-known principle of physics, it has not heretofore been applied to the field of thermogravimetric mass analysis. As indicated previously, at extremely elevated temperatures thermoconvection currents generated by the difference in temperatures between the test sample and the reactive gas may render a conventional thermogravimetric mass analysis reading inaccurate. The present invention provides a means of amplifying the change in the gravimetric mass by a factor of several hundred fold to assist in measuring the change as it occurs through a change in temperature, a change in sweep fluid velocity, a change in gas pressure, or a change in gas composition.

As indicated previously, the process of the present invention may be practiced with several different mechanical structures. These structures may be generally described by:
(a) angular displacement apparatus;
(b) null motor apparatus;
(c) reciprocating shaft displacement apparatus;
(d) reciprocating shaft null balance apparatus;
(e) radial displacement force apparatus;
(f) radial displacement apparatus.

In addition, each of the foregoing devices may be used with a variable speed motor for altering the apparatus mass of the sample.

The angular displacement apparatus may be summarized as a centrifugometric mass analyzer for measuring the continuous mass change of a test material subjected to selected temperatures and other fluid variables. The apparatus has a pair of angularly displaceable arms with a sample receiving means located at the end of one arm, and a known reference material receiving means located at the end of the other arm. The arms are balanced for rotation about a second axis of rotation. After initial balancing of the test sample with one or more known reference weights, the device is then spun or rotated about a first axis of rotation to subject the test sample to centrifugal force. Any change in the mass of the test sample then results in rotation of the pair of arms about the second axis of rotation. This angular displacement is then measured. The change in mass of the tested material may then be determined by a derivative value of the change of angular rotation. A variety of methods and means may be provided for measuring the angular displacement of the rotating arms.

The null motor apparatus may be differentiated from the angular displacement apparatus inasmuch as a null motor is connected to the support means for the two rotating arms. The null motor spins on the first axis of rotation with the pair of rotating arms, and any change in angular displacement about the second axis of rotation is immediately sensed by the null motor apparatus and a counter force or reactive force is generated to neutralize the angle of rotation and restore it to a center "nulled" position. The mass of the tested material and its change may then be determined by measuring the counter rotational force applied by the null motor to the angularly displaceable arms and its derivative value.

The reciprocating piston displacement apparatus may be distinguished from the above devices inasmuch as an angularly displaceable arm is provided for rotation only on one side of the first axis. A known and adjustable reference force is provided on the reciprocating piston placed along the first rotational axis and the angular displacement of the rotating arm and the tested solid exert a compressive or extensive force on the piston. A measurement means is used to measure the vertical displacement of the piston caused by the difference between the reference force and the force generated by the rotating arm and the tested solid. The displacement is then used to determine the mass of the tested solid by means of a calibration formula established prior to the operation through a series of mass measurements on various reference weights of known mass. A derivative value of the displacement is used to determine the corresponding derivative value of the change in mass as the tested solid is subjected to preselected temperature and fluid conditions.

The reciprocating piston null balance apparatus may be distinguished from the above reciprocating piston displacement apparatus inasmuch as a null device is connected to the reciprocating piston. The vertical displacement of the reciprocating piston is immediately sensed by the null device and a reactive force is generated to neutralize the displacement and restore it to its original null position. The mass of the tested solid and its change may then be determined by measuring the reactive force applied by the null device on the piston and its derivative value.

The radial displacement force apparatus may be distinguished from the foregoing devices inasmuch as only a single axis of rotation is used. The outwardly descending arm that connects the rotating shaft to the sample receiving means is normally perpendicular to the axis of rotation. As the sample receiving means is rotated, the radial force generated by the centrifugal force of the sample and sample receiving means is measured. As the sample undergoes a change in mass, the radial force is altered, and the mass change may be calculated from the change in displacement force.

The radical displacement apparatus may be distinguished from the radial displacement force apparatus inasmuch as the radial arm connected to the sample receiving means is allowed to reciprocate along a radial axis. In addition, reference weights and a null force generator may be added to at least partially offset the radial force generated by the rotating sample and sample receiving means.

In each of the foregoing embodiments the speed of the motor that drives the rotating shaft may be altered, thereby altering the apparent mass of the rotating sample. In the displacement apparatus, the speed may be decreased (as mass is gained) or increased (as mass is lost) to maintain apparent mass at a constant value. Likewise, with the null devices, the speed may be increased or decreased as the sample changes mass to balance a constant null force. Alternately, either the rotational speed, or the null force, or both may be altered to preselected values. Altering the preselected rotational speed may also be desirable to achieve a dynamic balance before mass change experiments are begun.

DETAILED DESCRIPTION OF THE ANGULAR DISPLACEMENT APPARATUS

Figure 13:
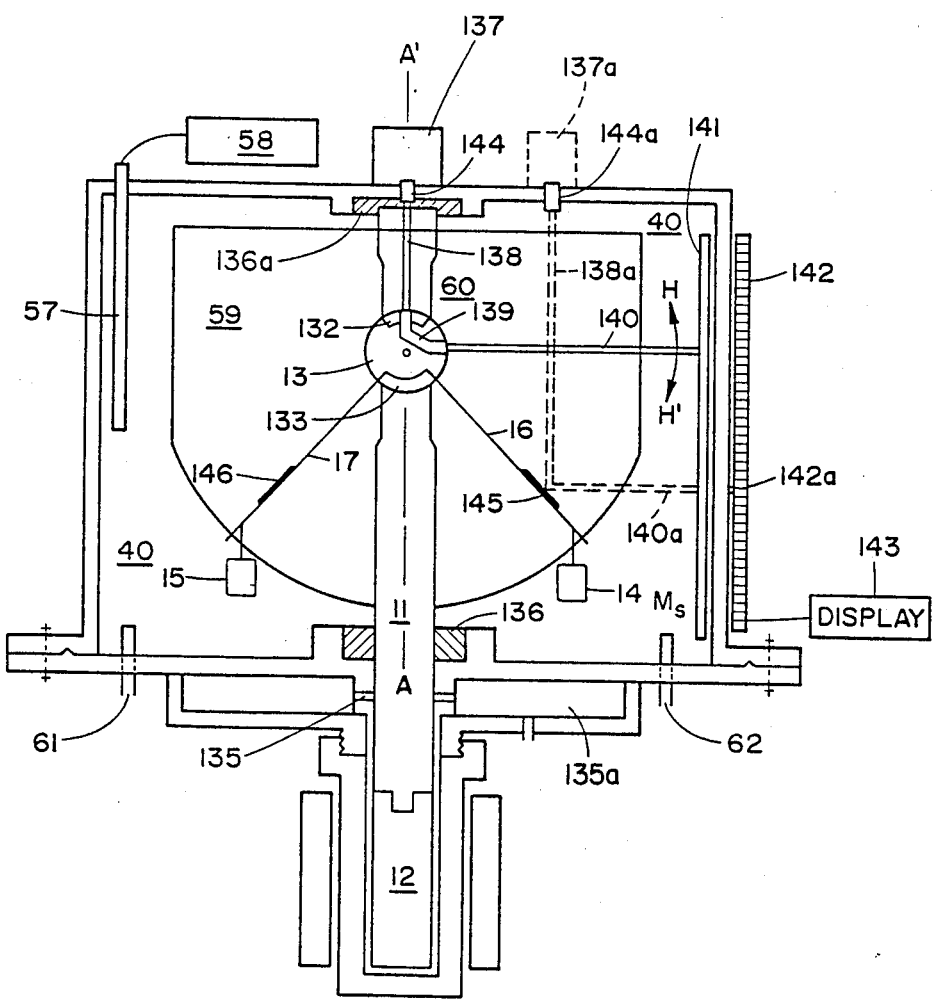
FIG. 13 is an alternate embodiment of the present invention having a plurality of display means for indicating the angular displacement of the rotor in an autoclave.

As illustrated in FIG. 1, the angular displacement apparatus has a first axis of rotation indicated by A—A' which is also the axis of rotation for shaft 11. A means for rotating shaft 11 is illustrated in FIG. 13 as motor means 12. A support means 13 is rotatably mounted on shaft 11 for rotation about a second axis indicated by $r_o$ in FIG. 1. The second axis of rotation is perpendicular to the first axis of rotation A—A'. A test material holding means 14 is illustrated in FIG. 1 in two states; a first static state in which holding means 14 is illustrated in solid lines, and a second dynamic state in which the holding means 14a is illustrated in dotted lines. A reference material holding means 15 is also illustrated in a first static state by solid lines, and in the second dynamic state 15a by dotted lines. A first outwardly extending arm 16 connects the support means or rotor 13 with the test sample holding means and a second outwardly extending arm 17 connects the reference material holding means to the support means or rotor 13. Also mounted on the support means or rotor 13 are a pair of compensator weights 18 and 19, which are once again illustrated in a static state in solid lines, and in a dynamic state in dotted lines as 18a and 19a.

Prior to the operation of the device, the apparatus is balanced by means of adjusting the mass and location of weights 20 and 21 to achieve both static and dynamic balance. A test sample is then placed in the test material holding means 14, and a reference material having a known mass characteristic is placed in the reference material holding means 15.

The apparatus is then rapidly rotated about axis A—A' as illustrated in FIG. 1. Any difference in mass between the test sample and the reference material is reflected by an angular displacement about the second axis of rotation $r_o$. As illustrated in FIG. 1, the test material has gained mass relative to the reference material contained in the container 15. Any change in mass of the tested sample is reflected by a corresponding change in the angular displacement. If for example, the test were one in which the test material were subject to high temperatures to determine what gaseous components might be driven off, the change in mass in the test sample contained in the test material holding means 14 would be reflected by an angular displacement in the opposite direction as the test sample loses mass.

Means for measuring the angular displacement are illustrated in FIG. 1 as a rotating indicator 29 and an angular displacement measurement means 27. Measurement means 27 may be mounted on the shaft 11 by means of vane 30, or may be fixably mounted within an enclosure such as the autoclave illustrated in FIGS. 13–16.

Figures 2A, 2B:
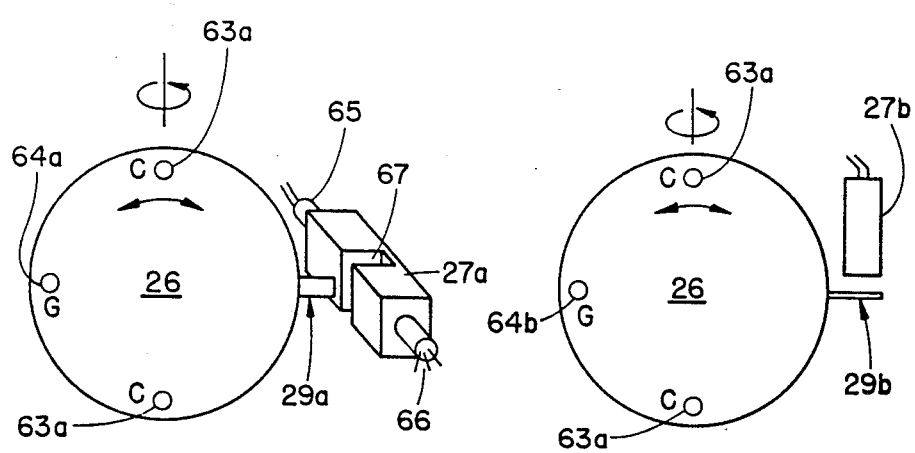
FIG. 2a is a diagrammatic illustration of a light emitter and flag used for measuring the angular displacement of the analyzer.
FIG. 2b is a diagrammatic illustration of a mutual inductance micrometer used to measure the angular displacement of the analyzer.
Figures 2C, 2D:
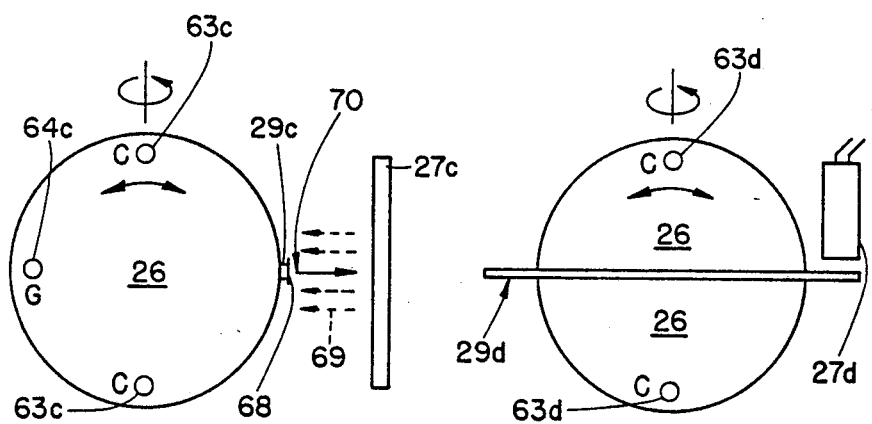
FIG. 2c is a diagrammatic illustration of an optical means including a mirror and a series of micro photo sensors used for measuring the angular displacement of the analyzer.
FIG. 2d is a diagrammatic view of an alternate embodiment using a mutual inductance micrometer mounted on the enclosure for measuring the angular displacement of the analyzer.
Figure 14:
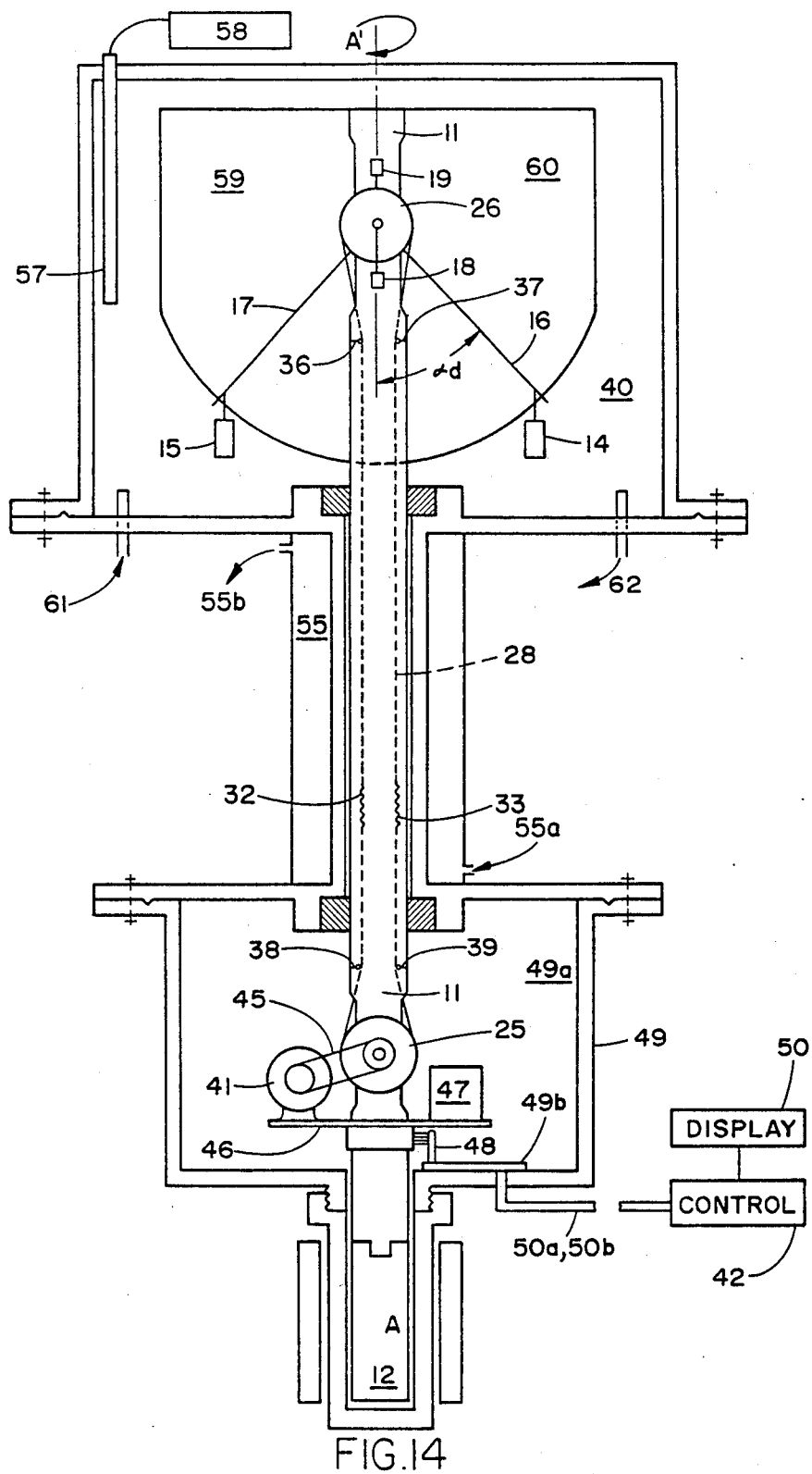
FIG. 14 is a partially cross-section frontal view of a null motor embodiment of the present invention illustrating its use in combination with an autoclave.
Figure 16:
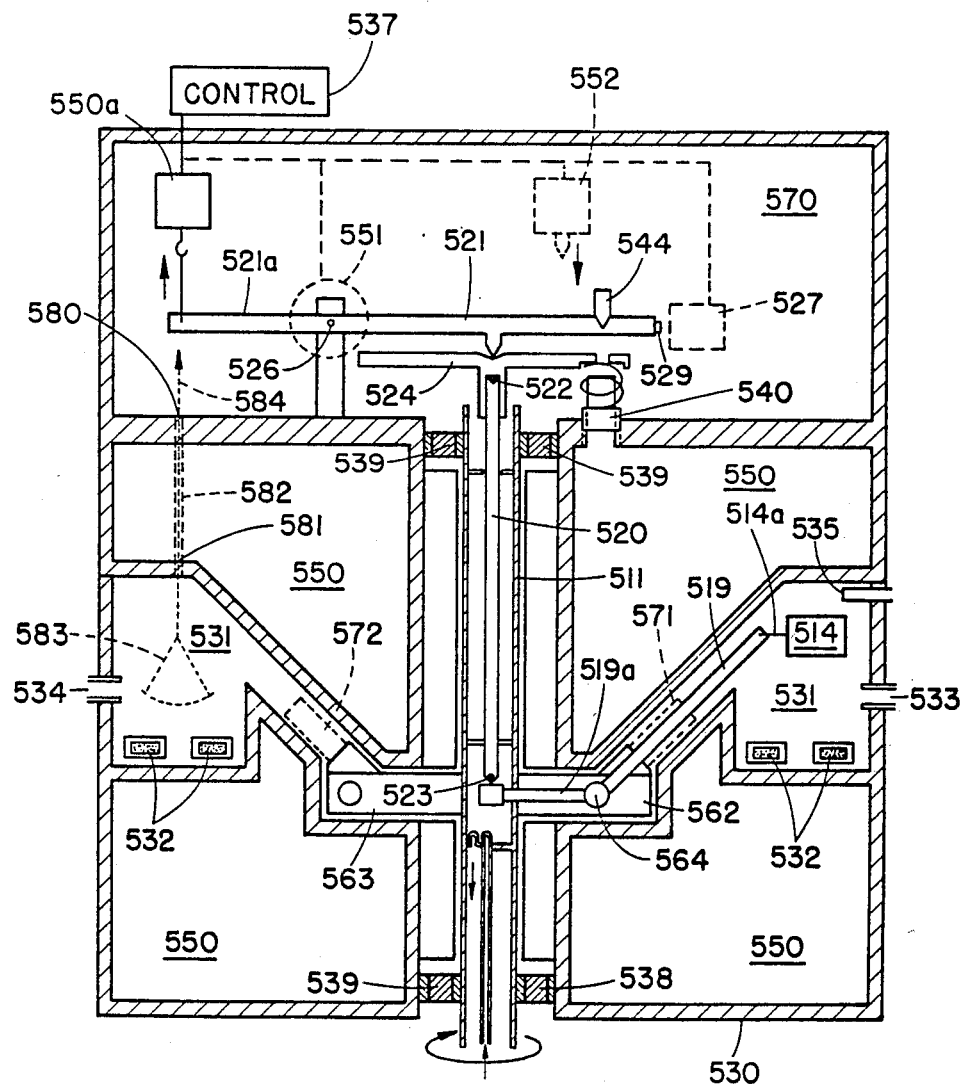
FIG. 16 is a cross-section and diagrammatic view of the analyzer illustrated in FIG. 7 as adapted for use in an extremely high temperature autoclave when the device may be used as a thermocentrifugometric mass analyzer, or a conventional thermogravimetric mass analyzer.

A variety of means for measuring the angle of rotation are illustrated in FIGS. 2a–2d to match the instrument to the specific conditions that will be tested or measured. When the instrument is used under extremely high temperature conditions, most electronic transducers would prove to be either inoperable or ineffective because of nonlinear response characteristics. In these cases, optical means such as those illustrated in FIG. 2a and FIG. 2c are considered to be more effective in accurately measuring the angle of rotation. FIGS. 13, 14 and 16 also illustrate other ways of removing the means for measuring the angle of rotation from the autoclave chamber to an external location.

In certain gas-solid and liquid-solid studies, the turbulence of the fluid medium, or the reaction between the fluid and the tested solid may render an optical indication of the angle of rotation extremely difficult to read. In such a case, an electronic transducer such as illustrated in FIG. 2b may be used in lieu of the optical means illustrated in FIGS. 2a and 2c. The various means for indicating the angle of rotation will be herewith discussed in detail with respect to the discussions of the various embodiments of the invention. As illustrated in FIG. 14, a dummy rotor 25 and the rotating indicator means 26 may have different sizes to amplify to reduce the apparent angular rotation about $r_0$. By decreasing the size of the dummy rotor 25 one is able to amplify the apparent angular rotation of rotor 26. This may be desired to improve the accuracy of the angular reading.

Rotor 26 and dummy rotor 25 are connected by means of a flexible drive member 28 which, in a practical application, may be a chain or flexible wire. The material is not important, but it is essential that all materials in the construction of the device illustrated in FIG. 1 be capable of withstanding the temperature and atmospheric conditions to which the test sample will be subjected. When used in the autoclave enclosure illustrated in FIG. 14, the temperatures to which the sample may be subjected may range from 200° to 2500° F.

Figure 10:
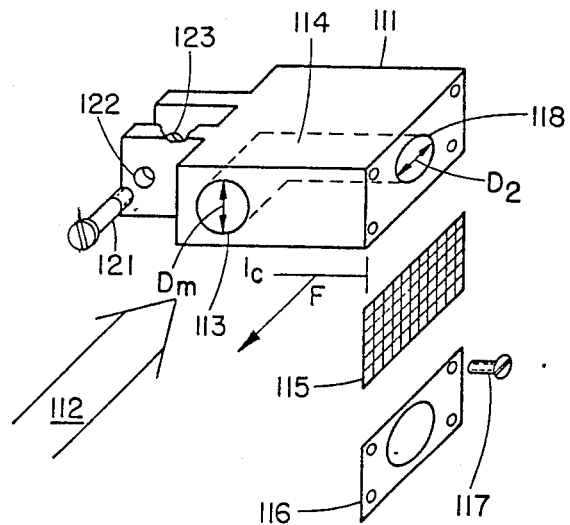
FIG. 10 is an isometric drawing illustrating a second embodiment for the sample retaining means that may be used with any embodiment of the present invention.

The rotor units illustrated in FIG. 1 require a precision design because the instrument is intended to be immersed in reacting fluid and generates the displacement needed for measurement of the mass of the test sample. The rotor disc is thin and light but needs to be relatively strong and rigid and may be constructed of metal, ceramics or quartz. Likewise, the outwardly extending arms 16 and 17 may be formed of metal, ceramic or quartz. The test material holding means 14 and the reference material holding means 15 may be small bowls, or baskets made of light and rigid material. Alternately, the material holding means may be formed with a specific configuration as illustrated in FIG. 10.

With respect to the angular displacement apparatus, the arms 16 and 17 are positioned at 90° from one another to ensure that the net moment of rotation generated by the two rotor arms vanishes in all displacement angles of $\theta$. This positioning also provides the maximum possible angle of displacement in either direction with respect to the net change in mass of the sample being tested. FIG. 1 schematically illustrates in dotted lines the rotational displacement, and Table I (following) mathematically describes the moment of rotation that causes the displacement. The net moment of rotation generated by the two rotor arms vanishes at all displacement angles $\theta$ when the rotor arms are positioned at right angles to each other. A net moment is generated by the baskets and their hangers when displaced. This moment is compensated for by a counteracting moment generated by the compensator weights 18 and 19. A very carefully calculated and designed compensator can reduce the resulting residual moment to a practical moment of zero over the entire range of the operating displacement angle $\theta$. As will be hereinafter described, the desired design angle is $-15°$ to $+15°$. A fine compensation for the net moment generated by the baskets and hangers can be adjusted by adjusting the positions and mass of compensator weights 18 and 19 along their support shafts 18b and 19b so that the residual moment of rotation can be kept as small as possible.

In one test version, the residual moment vanishes at both $\theta=0$ and $\theta=\pm 15°$ and is maximum at $\theta=\pm 7.5°$.

Other ranges of $\theta$ could be selected, but these could cause imbalance problems (when extremely large) or give insufficient displacement for reading (when extremely small). In addition, the relative angles of rotor arms 16 and 17 could be changed, but 90° has been selected as the optimum operating angle for this embodiment. For other embodiments, a different optimum operating angle may be selected.

When the residual moment of rotation is well compensated, the rotor assembly is dynamically well balanced at all displacement angles, and the ratio of the solid mass $M_s$ of the material to be tested (placed in the right hand side container illustrated in FIG. 1) to the reference mass $M_r$ of the reference material (placed in the left hand side container of FIG. 1) is related to $\theta$ by $$\frac{M_s}{M_r} = \frac{[\cos(45+\theta) + l_c/r_c]\sin(45+\theta)}{[\cos(45-\theta) + l_c/r_c]\sin(45-\theta)}$$

As illustrated in FIG. 1, Table I (following) and the above formula:

$M_s$ is the mass of the sample to be tested
$M_r$ is the mass of the reference material
$M_h$ is the mass of the hanger (14b, 15b)
$M_c$ is the mass of the container (14, 15)
$M_e$ is the mass of the compensator extension arm (18b, 19b)
$M_w$ is the mass of the compensator weights (18, 19)
$l_c$ is the length of the containers and hangers from their point of attachment to the rotor arms 16 and 17
$l_h$ is the length of the hanger arm between the rotor arm and the container
$l_w$ is the length of the compensator weights (18, 19)
$r_c$ is the radius of the rotor arms at the point of attachment for the hangers and containers 14, 14b, 15 and 15b
$r_e$ is the radius of the outer ends of the compensator weights 18 and 19
$r_d$ is the radius of the rotor disc 13
W is the speed of rotation of the first axis
T is the moment of rotation about the second axis

TABLE I
MOMENTS OF ROTATION $T/w^2$

| | |
|---|---|
| Rotor disc: | net:zero |
| Rotor arms: | net:zero |
| Container hanger | |
| $+ M_h r_c^2 [\cos(45-\theta) + 0.5(l_h/r_c)]\sin(45-\theta)$ | |
| $- M_h r_c^2 [\cos(45+\theta) + 0.5(l_h/r_c)]\sin(45+\theta)$ | |
| net: $-0.707 M_n r_c l_h \sin\theta$ | |
| Container | |
| $+ M_c r_c^2 [\cos(45-\theta) + 0.5(l_h r_c + l_c/r_c)]\sin(45-\theta)$ | |
| $- M_c r_c^2 [\cos(45+\theta) + 0.5(l_h r_c + l_c/r_c)]\sin(45+\theta)$ | |
| net: $-0.707 M_c r_c l_c [1 + (l_h/l_c)]\sin\theta$ | |
| Compensator extension arms (two) | |
| net: $+ 2\times(0.333) M_e r_e^2 [1 + (r_d/r_e) + (r_d/r_e)^2]\cos\theta\sin\theta$ | |
| Compensator weights (two) | |
| net: $+ 2X M_w r_e^2 [1 - (l_w/r_e) + 0.333(l_w/r_e)^2]\cos\theta\sin\theta$ | |
| Solid sample (RHS container) | |
| net: $+ M_s r_c^2 [\cos(45-\theta) + (l_c/r_c)]\sin(45-\theta)$ | |
| Reference mass (LHS container) | |
| net: $- M_r r_c^2 [\cos(45+\theta) + (l_c/r_c)]\sin(45+\theta)$ | |

The design and mass of the compensator weights illustrated in FIG. 1 is also based on the values selected for $r_d$, $r_e$, $r_c$, $l_w$, $l_c$, $l_h$, $M_e$, $M_c$ and $M_h$.

In the design of the compensator weights illustrated in FIG. 1, the residual moment of rotation is determined by:

$$\frac{T_{residual}}{w^2} = \frac{T_{net,\,container+hanger}}{w^2}\left[\frac{1 + T_{compensator+arm}}{T_{net,\,container+hanger}}\right]$$

Substituting the values of T listed in Table 1 gives:

$$\frac{T_{residual}}{w^2} = -0.707\, M_c r_c l_c [1 + (l_h/l_c) +$$

$$(M_h l_h/M_c l_c)] \cdot \sin\theta \cdot (1 - C\cos\theta)$$

in which compensator constant C is defined as:

$$C = \frac{M_w r_e^2 [[1 - (l_w/r_e) + 0.333(l_w/r_e)^2] + 0.333\, M_e r_e^2 [1 + (r_d/r_e) + (r_d/r_e)^2]]}{0.354 \cdot M_c r_c l_c [1 + (l_h/l_c) + (M_h l_h/M_c l_c)]}$$

The design of the compensator reduces to selecting a proper value of C so that $\sin\theta\cdot(1-C\cos\theta)$ remains reasonably small over the entire range of the operating displacement angle, $-15°<\theta<15°$. Two methods are tested in the following. In one, C is selected so that the residual moment vanishes not only at $\theta=0$ but also at $\theta=15°$. This is accomplished by chosing $C=1/\cos 15°=1.0353$. In the other, C is selected so that the integral of $\sin^2\theta(1-\cos\theta)^2$ over $0\leq\theta\leq15°$ is minimum. This least square fit gives $C=1.0207$. The values of $\sin\theta(1-C\cos\theta)$ at various $\theta$ are given below for the compensator constants determined by these two methods.

| $\theta$ | $\sin\theta\cdot(1-C\cos\theta)\times 10^3$ | |
|---|---|---|
| (degree) | C = 1.0353 | C = 1.0207 |
| 0 | 0 | 0 |
| 2.5 | −1.5 | −0.9 |
| 5.0 | −2.7 | −1.5 |
| 7.5 | −3.4 | −1.6 |
| 10.0 | −3.4 | −0.9 |
| 12.5 | −2.3 | 0.8 |
| 15.0 | 0 | 3.6 |

This indicates that the residual moment of rotation is relatively insensitive to the compensator constant over the range $1.021<C<1.035$, and either method is acceptable.

Once the compensator constant is selected, one can proceed to design the compensator using the above equation. In the test apparatus, with the following dimensions and mass constants, the above compensator constant equation provided $M_w=1.16$ g for $C=1.0353$ and $M_w=1.17$ g for $C=1.0207$:

$r_d=1.3$ cm;
$r_e=2.3$ cm;
$r_c=8.0$ cm
$l_w=0.75$ cm;
$l_c=3.0$ cm;
$l_h=1.0$ cm
$M_e=0.02$ g;
$M_c=0.3625$ g;
$M_h=0.0120$ g

Thus, a compensator weight of mass 1.16 to 1.17 g appears to be satisfactory for the test apparatus.

In this version of the test instrument, the linearity of the $M_r/M_s$ vs $\theta$ relationship was extremely good over the range of $0°<\theta<15°$, and provided the following relationship:

$$M_r/M_s = 1 - 0.012\theta$$

In this equation, it is understood that $M_s > M_r$ and therefore $\theta$ occurs in the direction of $M_s$. The same equation applies when $M_s < M_r$, with the left hand side of the equation replaced by $M_s/M_r$. Over the entire range of operable $\theta$, $0° < \theta < 15°$ in either direction, the measurable range of mass ratio is then given by $0.82 > (M_s/M_r) > 1.22$.

The range of mass ratio can then be translated into a window of mass measurement. When the reference mass is chosen to be the average of the initial and final masses of the tested solid, the apparatus is capable of measuring any mass change from a 33% decrease to a 49% increase relative to the initial mass. Larger mass changes can be accommodated by adding inert weights to both containers. For example, a mass change of 1 gram to zero can be measured by adding 2 grams of inert weights so that the total mass decreases from 3 grams to 2 grams, a 33% decrease. The range of mass ratio can be adjusted by varying the length of the container $l_c$ relative to the position of container pin $r_c$. Although $l_c/r_c$ greater than 0.4 is generally less desirable because of the resulting nonlinearity, any $l_c/r_c$ less than 0.4 increases both the linearity and the accuracy by narrowing the range of the mass ratio. Thus $l_c/r_c = 0.2$ gives $0.88 < (M_s/M_r) < 1.14$, or 23% decrease to 30% increase; and $l_c/r_c = 0.1$ gives $0.93 < (M_s/M_r) < 1.08$, or 14% decrease to 16% increase.

The accuracy in the measurement of the mass ratio against the displacement angle is affected by the residual moment of rotation, and its extent is determined by the ratio of the residual moment of rotation to the moment of rotation generated by the reference mass. When the compensator is designed as described above, a maximum of the ratio occurs at $\theta = \pm 7.5°$ and is given by $$\left(\frac{\text{residual moment}}{\text{moment by reference mass}}\right)_{max} = \frac{(2.5 \times 10^{-3}) M_c l_c (1 + l_h/l_c)}{M_r r_c (\cos 37.5 + l_c/r_c) \sin(37.5)}$$

In one embodiment of the invention, a test apparatus was constructed in which
$l_h = 1$ cm
$l_c = 3$ cm
$r_c = 8$ cm
the ratio then became:

$$\left(\frac{\text{residual monent}}{\text{moment by reference mass}}\right)_{max} = 2.0 \times 10^{-3} \cdot M_c/M_r$$

Therefore, insofar as the reference mass exceeded one-fifth of the basket mass, the error caused by the residual moment of rotation could be kept below one percent. As is apparent from the above formula, different proportions of $l_h, l_c, r_c$ and $M_c/M_r$ can also provide improved accuracy.

As illustrated in FIG. 1, in the angular displacement apparatus, the two rotor arms are placed at right angles to each other because the moment of rotation generated by these arms must be exactly compensated for over the entire range of the displacement angles. In the null point apparatus illustrated with respect to FIG. 3, this angle is determined by the total moment of rotation generated by the rotor arms, the mass containers and other parts mounted on the rotor, and need not be 90°. It has been found however that extremely small angles or extremely large angles cause a disturbance in the relative angular displacements of arms 16 and 17. This disturbance can then affect the accuracy of the mass measurements.

As illustrated in FIG. 1, the rotating shaft 11 has attached thereto a pair of vanes 30, 30a, which may be used to agitate the gaseous medium within an autoclave or other enclosure. A transducer means 27 is mounted on vane 30 to respond to flag means 29 which is fixably mounted to rotor disc 26. Transducer means 27 responds to the position of flag 29 to provide an electrical indication of the angular displacement of disc 26 and arms 16, 17. A balancing weight 31 is added to vane 30a to balance out the rotational unbalance caused by the angular displacement measuring device 27. A pair of slip rings 60 and 61 are provided to translate the electrical signals generated by transducer 27 from a rotary environment to a stationary environment. Slip ring 61 is mounted on shaft 11 and rotates with the shaft, while slip ring 60 is stationary, and mounted on a stationary portion of the enclosure. The operation of the transducer means 27 and flag 29 will be hereinafter explained with respect to FIGS. 2a-2d.

FIG. 2a illustrates a physical light obstruction flag 29a and is mounted on rotor 26. The light obstruction flag 29a traverses slot 67 in the transducer 27a as the rotor disc 26 is rotated. A light emitter 65 is used to provide a beam of light that transverses slot 67 and energizes photo-sensor 66. When in the central or nulled position, the light flag 29a partially obscures the light path between the light emitter 65, and the photo-sensor 66. As rotor disc 26 is rotated, however, a gradually larger or smaller signal is generated by photo-sensor 66.

Illustrated throughout FIGS. 2a-2d are gravity compensation weights 64a-64c, and centrifugometric compensation weights 63a-63d.

In the embodiment illustrated in FIG. 2b, a metal chip is mounted on the flag 29b. The transducer 27b then takes the form of a mutual inductance micrometer mounted for rotation on vane 30. While it is depicted in a vertical position in FIG. 2b, it should be understood that the positioning of the mutual inductance micrometer 27b could also be as illustrated in FIG. 1, adjacent the flag 29b. The output of the mutual inductance micrometer 27b is then conveyed to the slip ring 61 for output to the stationary slip ring 60 to a display and control means as will be hereinafter described.

As illustrated in FIG. 2c, a mirror 68 is mounted on the flag 29c. The transducer 27c takes the form of one or more parallel light sources 69 and a series of microphoto-sensors arrayed as illustrated at 27c in FIG. 2c. As disc 26 rotates, the mirror 68 reflects the light back as indicated by arrow 70 to energize one or more of the series of microphoto-sensors. As the rotor 26 is rotated, the relative path light beam 70 traverses the length of the series of microphoto-sensors 27c to provide an indication of the angle of rotation.

As illustrated in FIG. 2d, the flag 29 has been replaced with a circular disc ring, 29d, that serves a similar function to the metal chip mounted on flag 29b illustrated in FIG. 2b. The transducer 27d is again a mutual inductance micrometer that may be fixably mounted in the enclosure. Inasmuch as the flag 29d is a continuous circular ring, it will provide a steady output signal for the mutual inductance micrometer that is a function of the angular rotation of disc 26. As illustrated in FIG. 2b, the transducer 27b, is mounted on the rotating portion of the apparatus will provide a steady output that is a function of the distance between the metal chip and the inductance micrometer. If the transducer 27b illustrated in FIG. 2b is mounted on the enclosure, then the metal chip 27b would generate a series of pulses, the amplitude of which would vary as the disc 26 is rotated. By utilizing the angular ring illustrated in FIG. 2d, a steady output signal is derived which is a function of the angular rotation of disc 26.

DETAILED DESCRIPTION OF THE NULL MOTOR APPARATUS

Figure 3:
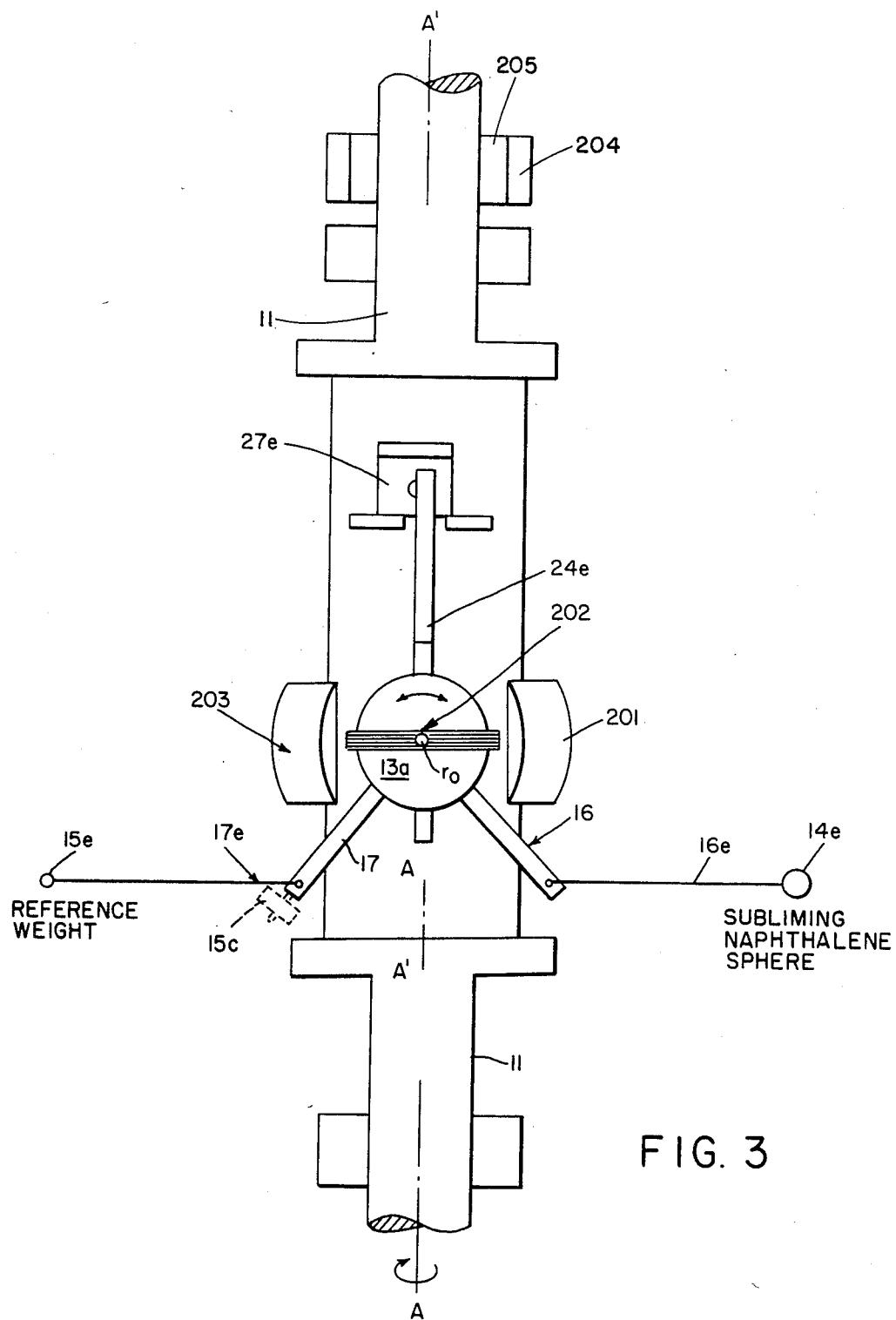
FIG. 3 is a partially cross-sectional frontal view of a null motor embodiment of the present invention used in a sublimation study.

FIG. 3 illustrates a second embodiment of the thermocentrifugometric analyzer wherein the angular displacement of the rotor 13a is opposed by a null motor apparatus which senses the angular displacement of the rotor and generates a counter reactive force to restore to its original position. The amount of reactive force necessary to maintain the rotor at the null point is then used to measure the mass of the sample. While the device illustrated in FIG. 3 is illustrated in a static position, it is understood that it rotates rapidly on shaft 11 about axis A—A' as was previously explained with respect to FIG. 1. Rotor arms 16 and 17 normally suspend a sample holder 14 and a reference weight holder 15 as was illustrated with respect to FIG. 1. In FIG. 3, however, the sample holder has been replaced with hanger 16e and a sublimating or "evaporating" sphere of naphthalene. Naphthalene is used as a typical example of a solid for which gaseous reaction studies might be desired. The reference weight holder 15 has been replaced with hanger 17e and a reference weight 15e. Alternately, the reference weight 15e may be replaced by a fixed and linearly displaceable weight 15c illustrated in dotted lines in the lower most portion of arm 17 in FIG. 3.

A coil 202 is formed about rotor 13a as will be hereinafter explained with greater detail with respect to FIG. 4. A current is supplied to coil 202 through slip ring commutators (not shown) as the shaft 11 is rotated. A fixed magnet 201 is mounted on one side of rotor coil 202, and a second fixed magnet or a variable electromagnetic coil 203 is placed on the other side of rotor coil 202. The current for coil 203 may also be supplied through a slip ring commutator in a manner similar to that supplied to coil member 202. In addition, if the loading of the device warrants, the magnetic field crossing the coil may be enforced by placing a highly permeable ferromagnetic material inside, but not in contact with the rotor 13a. Although not shown in FIG. 3, a magnetic carrier may be used to complete the magnetic circuit by connecting the outer poles of magnets 202 and 203. In addition, a polarized electromagnet may be used to strengthen the magnetic field surrounding the coil 202.

Application of a current to coil 202 will result in magnetic lines of force aligned along axis A—A'. The use of magnet 201 and magnet or coil 203 will tend to maintain the coil 202, and thereby rotor 13a in the position illustrated in FIG. 3. As a change in mass is experienced by sample 14e, the imbalance will generate a rotational moment about $r_o$ at the center of rotor 13a. If there is a change in mass wherein the sample 14e loses mass, rotor arm 16 will be displaced downwardly as illustrated in FIG. 3. If the reaction generates additional mass in the sample 14e, rotor arm 16 will be displaced upwardly. The relative rotational moment of rotor arms 16 and 17 about $r_o$ is opposed by the electromagnetic force generated on coil 202 subjected to the magnetic field generated by magnet 201 and magnet or coil 203. The relative rotational displacement of rotor 16a is measured by flag 29e, and transducer 27e in a manner similar to that previously described and illustrated with respect to FIGS. 2a–2d. Either a light detector, or a mutual inductance micrometer may be used. Any change in the position flag 29e will immediately be detected by transducer 27e, and communicated via slip ring commutators 204 and 205 to the electronic control circuitry for the thermocentrifugometric mass analyzer. Appropriate corrective currents will then be supplied through the stationary slip ring commutator 204, and the rotary commutator 205 to apply a corrective force to armature coil 202 that is mounted on rotor 13a. By measuring the change in current supply to coil 202 that is required to rebalance rotor 13a to its central nulled position, one is able to determine a functional value that is representative of the change of mass in the sample 14e.

The details of the device illustrated in FIG. 3 are further illustrated in FIGS. 4–6. The rotor 13a comprises an elongate cylinder in FIG. 4, or a disc as illustrated in FIG. 3 having a coil 202 wrapped around its center axis. Rotor 13a is supported for rotation by means of pins 208 and 209 in jeweled bearings 210 and 211. The jeweled bearings 210 and 211 are secured by jewel ring holders 212 and 213 which are threadably secured in apertures 214 and 215 (not shown) in shaft 11a as illustrated in FIG. 5. The use of pins 208, 209, and jeweled bearings 210 and 211, together with the threadable jewel ring holders 212 and 213 provide for very precise positioning of the rotor 13a within the enlarged shaft member 11a. The compensator weights 206 and 207 are secured to rotor 13a by means of rods 216 and 217. While end brackets 206 and 207 form part of the compensator weight, additional compensator weights may be provided as illustrated at 216–221 to compensate for the coil balance displacement flag or other structural features of the rotating parts of rotor 13a. The flag means 29e reciprocates within slot 67e as rotor 13a pivots about pins 208 and 209. In doing so, it varies the output of photo-sensor 66e. A light emitting diode, or other light emitter 65e is focused on photo-sensor 66e, and is partially occluded when in the central balanced or nulled position by means of flag 29e.

As illustrated in FIG. 5, shaft 11 contains an enlarged portion 11a for containing the rotor 13a. Formed within the enlarged shaft portion 11a is a transducer mounting plate 222 having a slot 223 formed therein for receiving the flag 29e. In addition, when used in an extremely high temperature environment, the rotor is equipped with high temperature shielding or radiation reflecting means 224 which is more fully illustrated in FIG. 6. The conical portion 11b of shaft 11 is protected by means of insulation 224a and a radiation reflector 224b to prevent the intense heat generated by the high temperature autoclave from reaching the electrical components mounted within the enlarged shaft 11a. The need for the radiation reflector and insulation will be more fully illustrated with respect to the device illustrated in FIG. 15.

An alternate embodiment for the null point apparatus for measuring the change in mass in accordance with the principles of the present invention is illustrated in FIG. 14. As illustrated in FIG. 14, a rotary disc 13, the support arms 16 and 17 and the baskets 14 and 15 are essentially the same as those described previously with respect to FIG. 1. Although it is illustrated in a static position, in operation it is rapidly rotated about axis A—A' by means of shaft 11 and motor means 12. The relative angular displacement of rotor 13 is transferred by the flexible linkage 28 to dummy rotor 25 which is now mounted below the autoclave chamber 40. The flexible drive means 28 is guided by means of rollers 36, 37, 38 and 39 within shaft 11 to provide a relatively friction free transfer of the relative angle of rotation from rotor disc 13 to dummy disc 25. Tensioning means 32 and 33 maintain appropriate tension level on flexible drive means 28. In the preferred embodiment, a thin wire chain was used to transfer the angular rotation from rotor 13 to dummy disc 25. As indicated previously with respect to FIG. 1, the angular displacement can be read directly by optical means, or can be converted into an electrical signal by hydraulic, electrical, magnetic, or optical means. In the null point apparatus illustrated in FIG. 3, however, the angular displacement generates an electrical signal in a displacement measuring means 43 (illustrated in FIG. 11). Control means 42 is responsive to the signal and responds by energizing motor means 41 to generate a reactive force along drive means 45 to the dummy rotor 25. The reactive force is then transmitted by a flexible drive means 28 to the rotor 13. In the null point apparatus, motor 41 is a two poled DC motor placed on a supporting frame 46 which is fixed on rotating shaft 11. A compensator weight 47 is provided to maintain an effective balance for the null point apparatus during the high speed rotation of shaft 11. A pickup brush 48 is used to transfer the input and output signals and power for motor means 41 from the stationary support 49b to the rotating shaft 11. The electrical signals picked up by brush 48 are transmitted by a control line 50b to the control unit 42.

Figure 11:
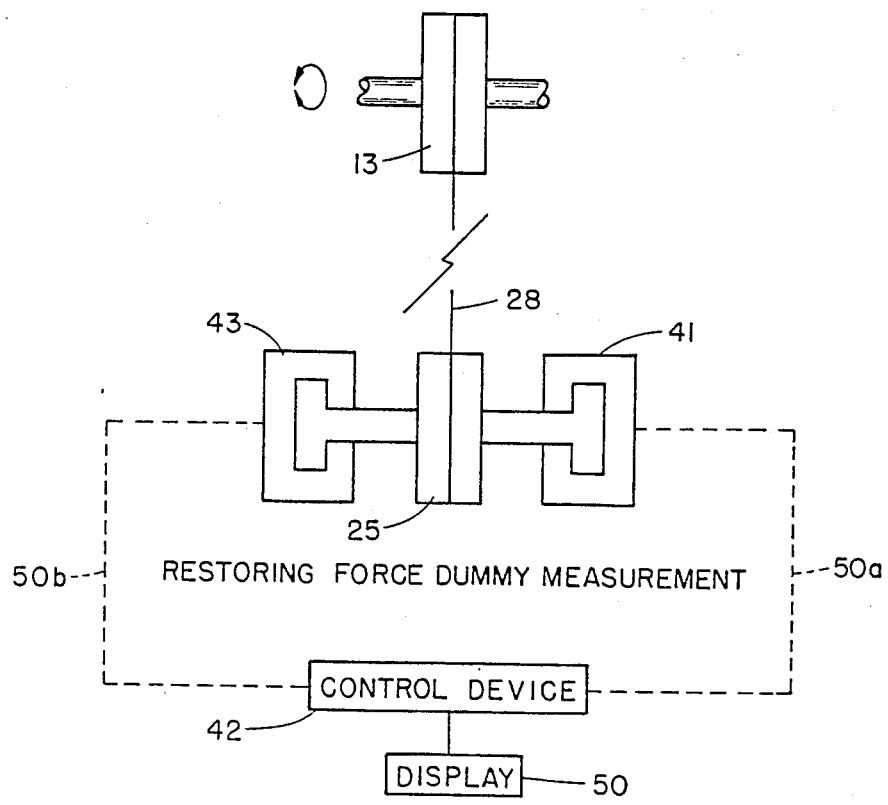
FIG. 11 is a schematic illustration of a null motor embodiment of the analyzer illustrated in FIG. 14.

A schematic of the null point apparatus is illustrated in FIG. 11 wherein 13 refers to the rotor, 25 the dummy rotor, 41 the motor means, and 43 the displacement measuring means for measuring the angular displacement of dummy disc 25. The signal generated by measuring means 43 is transmitted by control line 50b to control device 42 which energizes the motor 41 through control line 50a, to restore the angular rotation of dummy disc 25 to its central "nulled" position. The restoring force is then transmitted along the flexible means 28 to rotor 13 when the speed of rotation is varied, the null force is related to the speed of rotation. This relationship will be further explained hereinafter in the Detailed Description of the Speed Regulation Mode.

As illustrated in FIG. 14, the invention is particularly adapted for use in a heated autoclave unit for high temperature reaction studies. The instrumentation chamber 49a can be protected from being overheated by providing a cooling jacket 55 having a source of cooling water at 55a and an outlet for the coolant at 55b. This not only provides for cooling of shaft 11, but also insulates the autoclave unit 40 from the instrumentation chamber 49a. The autoclave unit 40 utilizes conventional means for heating the interior of the chamber to extremely high temperatures. These studies may be conducted at any temperature from 200° to 2500° F. An instrumentation probe 57 is connected to a control means 58 for maintaining the autoclave at the desired thermal temperature(s). In addition to the thermocentrifugometric analyzer, the rotating shaft 11 also has a pair of agitator blades 59 and 60 to enhance gas mixing within the autoclave. In addition, electrical heating elements may be placed in the agitator blades 59 and 60 to assist in maintaining the interior of the autoclave at a constant temperature. A gas inlet conduit 61 and a gas outlet conduit 62 are provided for admitting and discharging reactive gases when it is desired to conduct a mass analysis with a specific gas in lieu of ambient atmospheric air. If desired, the gas inlet may be placed directly in line with the dynamic position of containers 14 and 15 to direct high speed impingement of the gas supplied through conduit 61 into the path of container 14. In addition, chamber 40 may be pressurized by means of conduit 61 and 62 to provide mass analysis under high pressure gas conditions.

The control device 42 is equipped with a suitable display 50 for indicating the amount of the reactive force generated by motor means 41 and applied to the rotor disc 13. Alternately, it may display a derivative signal which is indicative of the change in mass indicated by the amount of reactive force needed to maintain dummy disc 25 and rotor 13 and their central "nulled" position.

DETAILED DESCRIPTION OF BALANCE BEAM APPARATUS

In the third embodiment of the present invention, one or more rotor arms are provided which are pivotally biased against a balance beam by means of a reciprocating piston connected between the beam and the rotor arm. Means are provided for calibrating the balance beam to provide a known reactive force for the sample as it is subjected to centrifugal force. After a first reference force is generated by the balance beam, to affect the apparent mass of the sample, any change in mass in a test sample will be measured directly by a change in the balance beam position.

The reciprocating piston displacement apparatus may be distinguished from the above devices inasmuch as an angularly displaceable arm 319 is provided only on one side of the rotational axis A—A' as was previously described with respect to FIGS. 1 and 3. A known and adjustable reference force is provided on the reciprocating piston 320 that is aligned along the first rotational axis A—A', and the angular displacement of the rotating arm and tested solid exert a compressive or extensive force on the piston. A balance beam measurement means 321 is used to measure the vertical displacement of the piston caused by the difference between the reference force and the force generated by the rotating arm and the tested solid. The displacement is then used to determine the mass of the tested solid by means of a calibration formula established prior to the operation through a series of mass measurements on various reference weights of known mass. A derivative value of the displacement is used to determine the corresponding derivative value of the change in mass as the tested solid is subjected to preselected temperature and fluid conditions.

Figure 7:
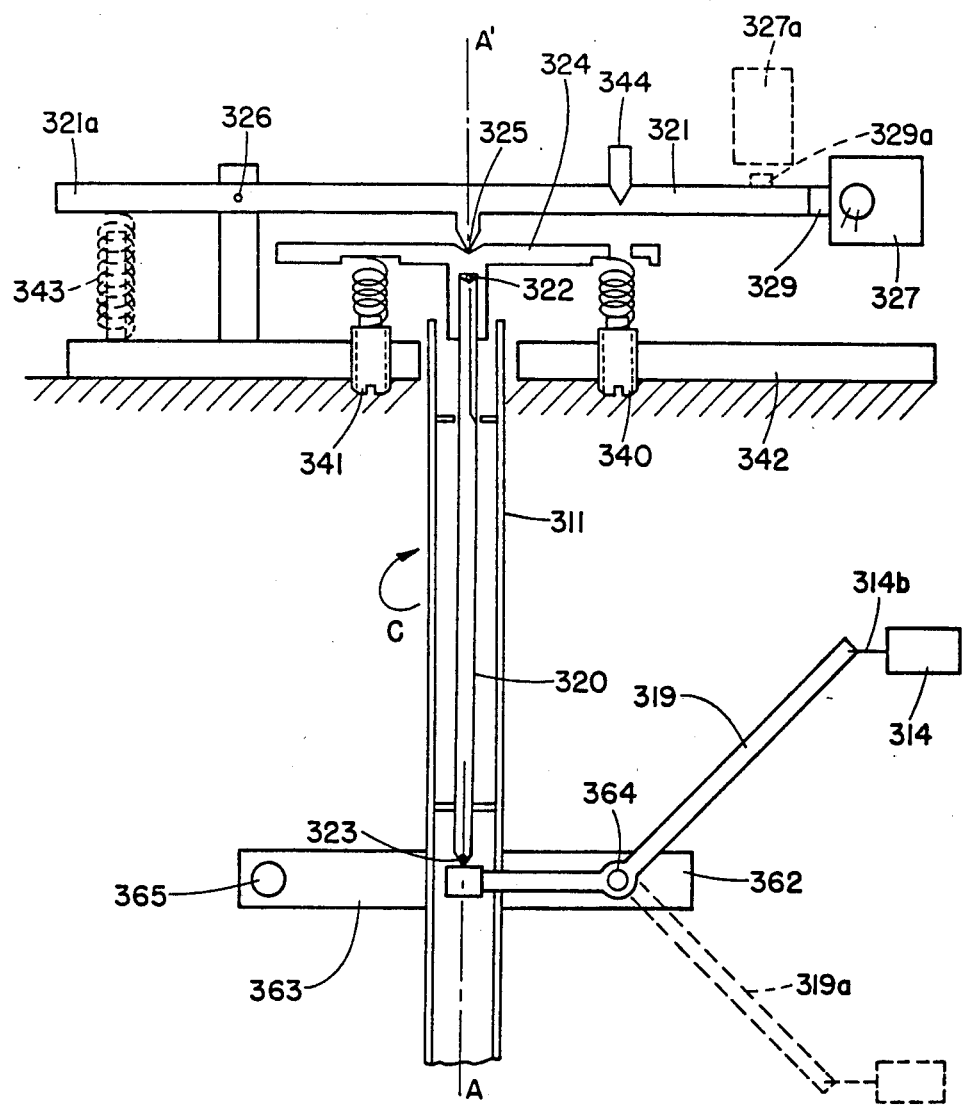
FIG. 7 is a cross-sectional and diagrammatic view of another embodiment of the invention utilizing a reciprocal rod and balance beam.

As indicated in FIG. 7, the displaceable arm 319, may be of one-branch construction as illustrated by the solid lines, or a second branch may be added as illustrated by the dotted lines 319a. The material to be tested is placed in basket 314 which is suspended from arm 319 by means of hanger 314b. The rotational movement of shaft 311 is imparted to the reference container by means a motor as illustrated in FIGS. 13 and 14. Support arm 362 and 363 may also serve as circulatory vanes to agitate the fluid or gaseous mediums surrounding the sample container 314. The balance weight 365 is provided on arm 363 to compensate for the relative mass of arm 319 and 319a, and the weight of basket 314. As the device illustrated in FIG. 7 is rotated about axis A—A', a rotational moment is generated about axis 364 urging the rotor arm 319 outwardly and displacing the reciprocating shaft 320 upwardly as illustrated in FIG. 7. Reciprocating shaft 320 is provided with bearing means 322 and 323 which are used on either end of reciprocating rod 320 to minimize the frictional drag that may be generated between the rotation of rotor arm 319a caused by the rotation of shaft 311, and the stationary position of balance beam 321. To further assist in translating the rotary forces to a stationary balance beam, an adjustable platter 324 is provided between the reciprocating shaft 320, and the balance beam 321. A jeweled bearing 325 is used between the platter and the balance beam to translate the vertical movement of reciprocating rod 320, to the angular movement of balance beam 321, about axis 326. The relative movement of balance beam 321 may be detected by transducer 327 or 327a (illustrated in dotted lines) in a manner previously illustrated with respect to FIGS. 2a–2d. As illustrated at 327, a photo-optical transducer is used with a flag 329 attached to the end of balance beam 321. Alternately, a metal chip or magnet 329a may be attached to the balance beam to activate a micro inductive coupler 327a.

A plurality of spring loaded adjusting screws illustrated at 340 and 341 in FIG. 7 are used to precisely align platter 324 in a horizontal position with respect to stationary support means 342.

In operation of the device illustrated in FIG. 7, the mass $M_s$ of the test sample is compensated for by means of an adjustable spring means 343 which exerts a compressive or upward force on balance beam 321a. An adjustable weight 344 is moved along balance beam 321 to a predetermined position that is determined by the weight of the sample to be placed in test sample basket 314. A predetermined position of weight 344 is calculated for a variety of rotational speeds for shaft 311 and a variety of weights in said $M_s$ that may be placed in basket 314. Thus, in the operation of the device, when the shaft 311 has reached its predetermined rotational speed, with mass $M_s$ in basket 314, the balance beam will be balanced. The force generated by spring balance 343, and the position of displaceable balance weight 344 is balanced against the apparent mass of the rotation sample at a predetermined speed. As the sample $M_s$ gains or loses mass in its reaction with the fluid or gaseous medium surrounding basket 314, the rotational force is first generated about axis 364, which is translated into vertical reciprocation of reciprocating shaft 320. The vertical movement is then translated through platter 324 to balance beam 321, and measured by transducers 327 or 327a.

Figure 8:
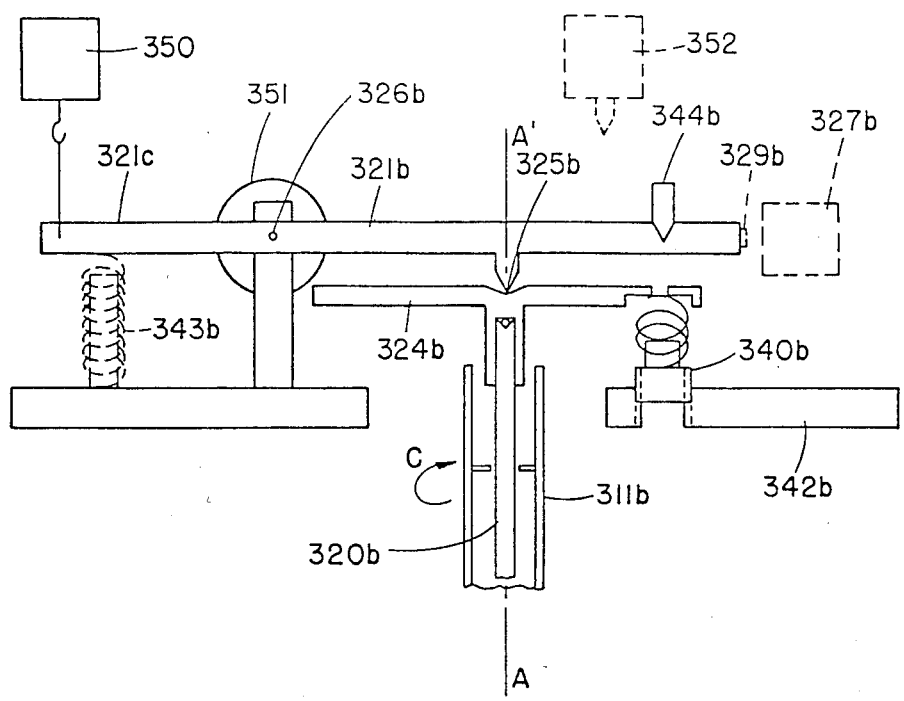
FIG. 8 is a diagrammatic view of several alternate means that may be used to generate compensating forces to "null" the balance beam illustrated in FIG. 7.

The embodiment illustrated in FIG. 8 generates reciprocal forces along reciprocating shaft 320b in a manner identical to that previously described with respect to FIG. 7. The forces generated along balance beam 321b, however, are different from those generated along balance beam 321 and 321a illustrated in FIG. 7. A variety of means illustrated as 350, 351 and 352 may be used to provide a compensating or restoring force to the balance beam to maintain it in a central or nulled position. The amount of force necessary to restore the balance beam to its nulled position may also be derived by means of more than one technique.

As was previously illustrated with respect to FIG. 7, the upwardly generated force at point 325b on balance beam 321b is opposed by spring means 343b, insofar as the force is generated by the mass of arm 319 and hanger 314. The force generated by $M_s$ at the rotational speed and weight selected and placed in hanger basket 314 is compensated for by adjustable weight 344b. Means 350, 351 and 352 all provide means of generating additional compensatory forces to restore the balance beam to a central nulled position. In a first version of the null device, the transducer 327b detects movement of a metal or magnetic chip 329b on the balance beam 321b. As movement of the balance beam is detected, a compensating force is applied by any one of the means 350, 351, or 352. The device illustrated at 350, is an adjustable point gravimetric balance which will apply a counter force to spring 343b, depending upon the electrical force transmitted to it by appropriate control circuitry (illustrated in FIGS. 11 and 14). Alternately, a motor 351 may be used to exert a rotational torque about axis 326b on balance beam 321b. In a third embodiment of the null point balance beam apparatus, a compressive type null device 352 may be used in lieu of or simultaneously with the adjustable weight 344b to provide an adjustable downwardly displaceable weight on balance beam 321b. As the balance beam 321b is deflected upwardly or downwardly by a change of mass $M_s$ in container 314, the amount of force generated by the compressive type null device 352 changes to restore the balance beam 321b to a center nulled position.

Alternately, the device 351 illustrated as a motor in FIG. 8, may be replaced by a displacement measuring means to measure the angular displacement of balance beam 321b. The control device (not shown) will then cause a compensating force to be generated by means 350 or 352.

While an electrical means has been disclosed in FIGS. 11 and 14, it should be understood that the compensating forces generated by means 350, 351 and 352 could be created electrically, hydraulically, magnetically, or pneumatically, as desired. Each of the respective modes of operation has distinct advantages, depending upon the operating parameters and conditions in which the device will be operated.

Figure 17:
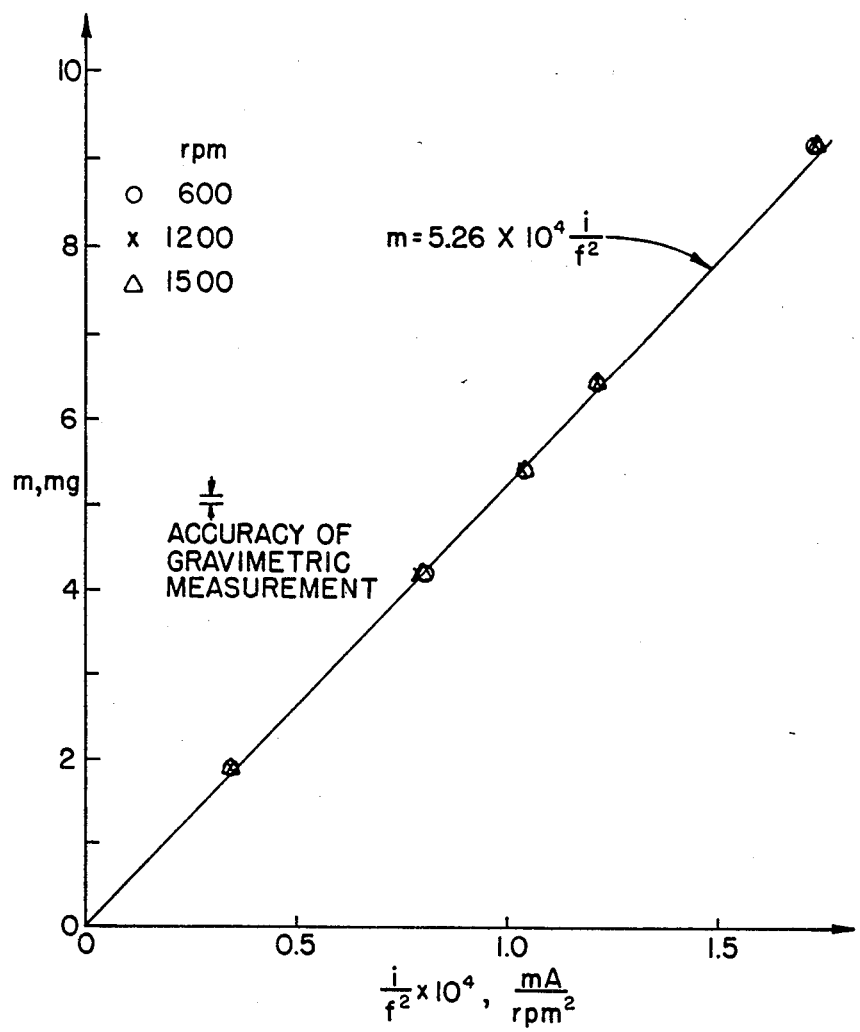
FIG. 17 is a graph illustrating the accuracy of a null motor thermocentrifugometric mass analyzed for the $M_s$ values and rotational speeds listed in Table 2.

The test results from a thermocentrifugometric mass analyzer using a null motor to generate a counter restoring force is illustrated in FIG. 17, using the $M_s$ values and rotational speed listed in Table 2.

TABLE 2

| Test solid mass* $M_s$ | Null current required (milliamperes) | | |
|---|---|---|---|
| (milligrams) | 600 rpm | 1200 rpm | 1500 rpm |
| 1.9 ± 0.1 | 12.5 | 50.0 | 79.0 |
| 4.2 ± 0.1 | 29.0 | 115 | 180 |
| 5.4 ± 0.1 | 37.5 | 150 | 235 |
| 6.4 ± 0.1 | 43.5 | 175 | 275 |
| 9.2 ± 0.1 | 62.5 | 250 | 390 |

*measured by a conventional gravimetric balance with an accuracy of 0.1 milligrams.

As illustrated in FIG. 17, using the null motor balance, the null current required, i, is proportional to the test solid mass, $M_s$ and inversely proportional to the square of the rotational speed, f, or $$i = (1/K)M_s f^2$$

or $$M_s = K(i/f^2)$$

in which the proportionality constant, K can be calculated from the geometry of the coil and the magnetic field strength. However, when the magnetic field strength is difficult to measure, a plausible alternative to the calculation procedure is to determine it from a linear regression of preselected test data. Thus for this particular balance $$K = 5.26 \times 10^4$$

when i is in milliamperes, $M_s$ is in milligrams and f is in rpm. As illustrated in FIG. 17 the gravimetrically measured $M_s$ is plotted against $i/f^2$.

As can be seen in FIG. 17, the accuracy of a test prototype null-motor balance exceeds 0.1 milligrams. The final production version of the device should result in a thermocentrifugometric mass analysis having an accuracy in the nanogram range.

DETAILED DESCRIPTION OF THE SPEED REGULATION MODE

The speed regulation mode of operation is adaptable for mass measurement processes wherein the centrifugal force generated by the rotating test solid is balanced against a reference force which is independent of the rotational speed. This mode of operation is therefore primarily applicable to the null motor embodiment, the reciprocating shaft null balance embodiment, and the radial displacement embodiment which will be hereinafter discussed. While this embodiment may be used on the angular displacement embodiments, it is not particularly useful inasmuch as the reference weight is subjected to the same centrifugal force field as the test sample. The principle of the speed regulation mode involves the change in the apparent mass of the test sample by changing the rotational speed of the device. In both modes of operation, the centrifugal force generated by the rotating test sample is balanced against a measurable reactive force independent from the rotational speed, or:

| Centrifugal force of test solid proportional to $rpm^2$ | = | Measurable reactive force at least partially independent of rpm |
|---|---|---|

The null force embodiments require two separate control circuitries, one for the null motor (or the balance beam motor) to generate the reactive force, and the other for the driving motor to regulate the speed of rotation at a preselected value. In comparison, only the driving motor control circuitry is required for the speed regulation mode. Both modes of operation require a motor with a precisely regulated speed. Synchronous motors are commercially available with virtually any accuracy desired for thermocentrifugometric analysis. Many manufacturers state that their speed regulation accuracies are better than 0.01 rpm at several preselected target speeds in the range of thermocentrifugometric analysis applications. Synchronous motors, however, require a precision frequency power source for precise speed control, and this precision frequency power source is usually quite costly.

Figure 18:
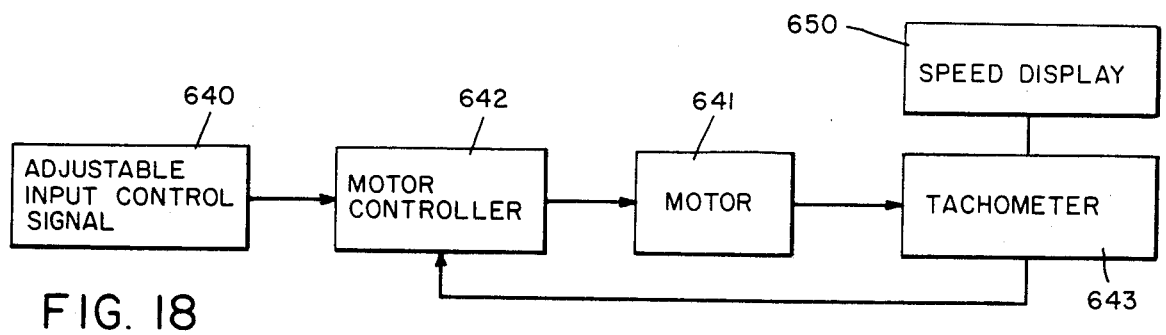
FIG. 18 is a diagrammatic illustration of a motor control circuit used to control the speed of rotation of the analyzer.

DC motors are available with current design and control technologies available that will maintain the speed regulation within a range of 0.05% under various load conditions. This corresponds to speed regulation within two to three rpm at 5000 rpm, and a mass measurement accuracy of 0.1% at 5000 rpm. This level of speed regulation accuracy is felt to be reasonable for most mass measurement purposes of thermocentrifugometric analyzers in both null mode environments, and speed regulated modes. The sample control system for such a motor is set forth in FIG. 18 wherein an adjustable input control signal 640 is used to set the initial speed of rotation. Speed regulated DC motors are available commercially with built-in tachometers such as tachometer 643. This tachometer may be mechanical, electrical, or optical. A variety of commercially available electronic control circuitries such as 642 are also available (SCR, SPT, etc.) and are used to provide a regulated current to the motor 641. The input set speed may be accomplished by means of an adjustable input control signal 640 which may comprise a potentiometer which bridges a reference voltage with a tap to the input of the motor controller 642.

In the null motor regulation mode, the operator only needs to select a potentiometer setting or the adjustable input control signal 640 to set the rotation of speed and let the controller maintain the speed at that particular value throughout the entire period of test. On the other hand, in the speed regulation mode, with the null force fixed, a control means needs to continuously detect the displacement and reset the input control signal 640 until the null point is reached. At this point, the rpm is read on speed display 650. If a constant value of null force is supplied, and the sample undergoes a change in mass, a further adjustment of input control signal 640 will be necessary for each change in mass.

Figure 19:
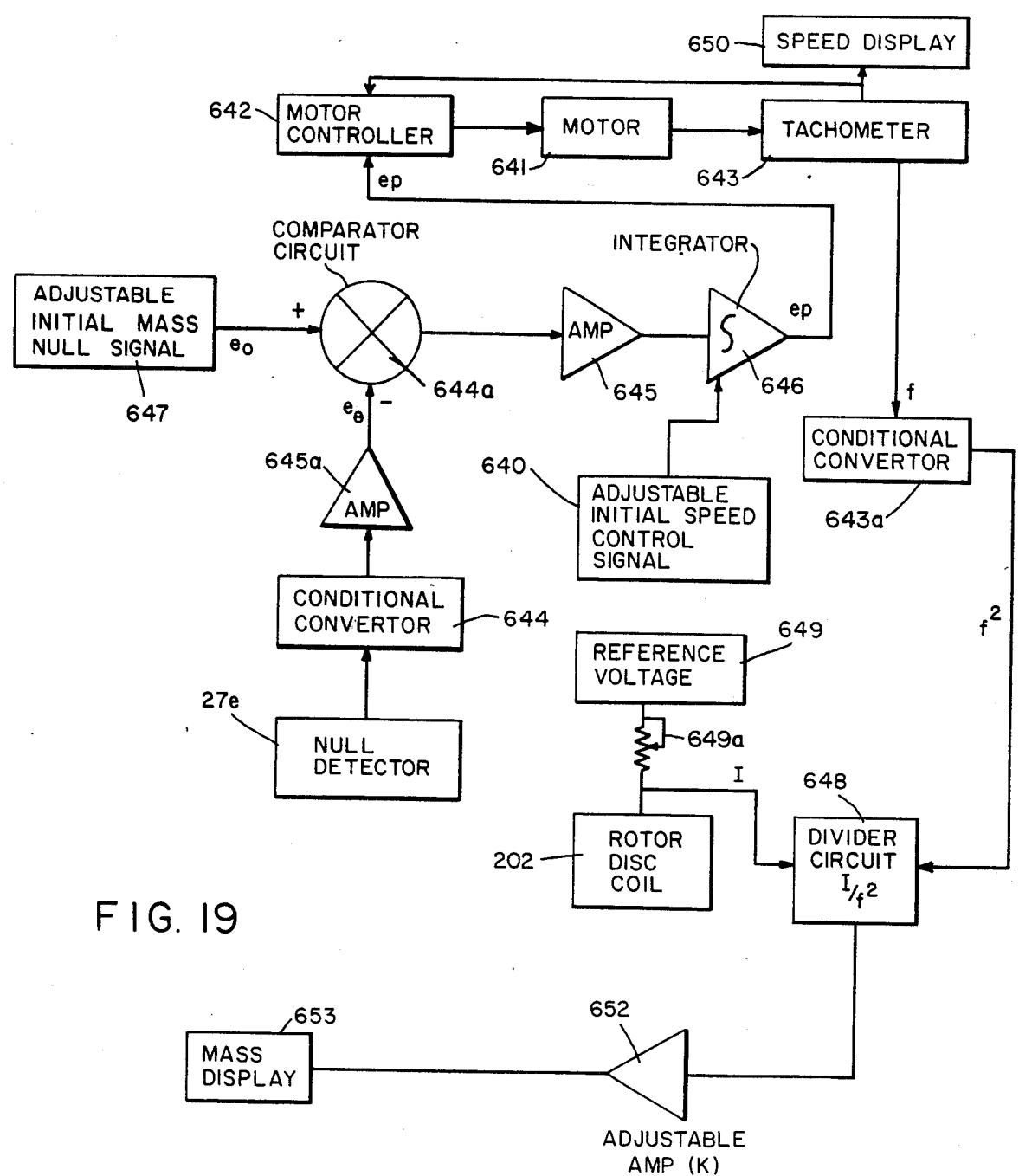
FIG. 19 is a diagrammatic illustration of a combined motor control and null balance control circuit used to rebalance the analyzer through a change in the speed of rotation.

FIG. 19 illustrates a control circuit for combining the null force embodiment mode and the speed regulation mode. The null force mode is equally applicable to the angularly adjustable null force embodiment illustrated in FIG. 3, the reciprocating rod embodiment illustrated in FIG. 8, and the radial displacement mode illustrated in FIG. 22. While the precise details of the circuit illustrated in FIG. 19 will vary from embodiment to embodiment, FIG. 19 will be explained with reference to the embodiment illustrated in FIG. 3. In this embodiment, the adjustable initial mass null signal 647 provides a reference voltage $e_0$ to comparator circuit 644a. Simultaneously, the null detector 27e which, as illustrated in FIG. 3, provides an output signal to conditional converter 644. A conditional converter is used to convert the output current or voltage from the null detector to a consistent control voltage for amplifier 645a. As illustrated in FIGS. 2a–2d, a variety of null detectors may be used to indicate the rotation of rotor 13 or 13a. Depending upon the type of null detector used, the output may vary, thus requiring the conditional converter 644, to provide a consistent output voltage to comparator 644a. The output voltage $e_\theta$ is indicative of the angular position of the rotor 13. Comparator circuit 644a is used to calculate $e_\theta - e_0$ where $e_0$ is the null voltage and $e_\theta$ is the angular displacement signal converted to voltage. If $e_\theta$ is greater than $e_0$ (or $e_0 - e_\theta$ is less than zero) it means that the rotational speed is too high, and therefore the voltage input $e_p$ to the driving motor control circuit has to be reduced in order to lower the motor speed. Amplifier 645 is provided to adjust the sensitivity of the driving motor control circuit with respect to the angular displacement signal. Integrator 646 allows only a small variation in the voltage input ($e_\theta - e_0$) to the driving motor control circuit 642. The adjustable initial speed control signal 640 is used to set the initial rotational speed of the device.

The adjustable initial mass null signal may be a potentiometer bridged across a reference voltage, with the tap of the potentiometer providing the initial mass null signal $e_0$. The initial mass null signal 647 is set while the device illustrated in FIG. 3 is rotated, to initially balance the apparatus without the test material.

The voltage input $e_p$ then adjusts the speed of motor 641 via motor controller 642 in response to the movement of flag 29e sensed by null detector 27e. The motor output speed, as determined by tachometer 643, is then fed to conditional converter 643a as illustrated in FIG. 19. The signal f arriving at conditional converter 643a is representative of the frequency of motor 641. Inasmuch as the tachometer 643 can be any commercially available tachometer, and may provide the signal f in current, voltage, or digital form, a conditional converter 643a is provided to provide a voltage output that is a square ($f^2$) for the speed of rotation of motor 641.

Simultaneously, a reference voltage 649 is divided by potentiometer 649a and fed to the rotor disk coil 202. The current flow (I) through rotor disk coil 202 is also provided to divider circuit 648 with the current (I) supplied as the enumerator, and signal $f^2$ as the denominator. The output of divider circuit 648 is then multiplied by an adjustable constant in amplifier 652 to provide a functional value of the output signal from divider circuit 648. The output of adjustable amplifier 652 is then displayed on a mass display readout 653.

As was indicated previously with respect to Table II and in graph 17, the equation for derivation of the mass of the sample may be illustrated as:

$$M_s = K(i/f^2)$$

In the above equation, the proportionality constant, K can be calculated from the geometry of the coil and the magnet field strength from magnets 201 and 203. This constant, K, is provided by adjustable amplifier 652. However, when the magnetic field is difficult to measure an alternative to the calculation procedure is to determine the constant K from a linear regression on preselected test data. This was done with respect to the data in Table II to derive FIG. 17.

DETAILED DESCRIPTION OF THE RADIAL DISPLACEMENT APPARATUS

Figure 20:
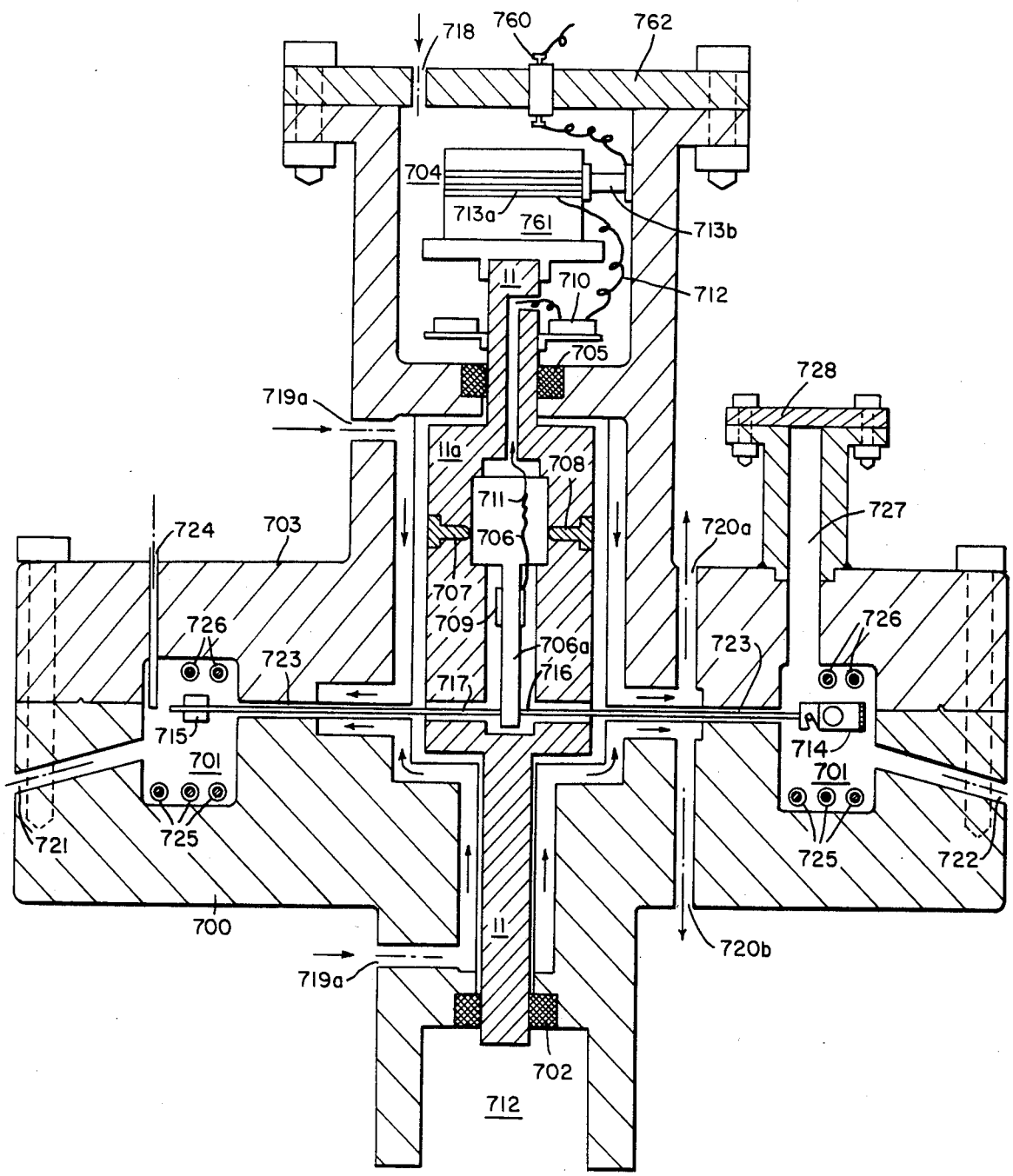
FIG. 20 is a partially cross-sectional and diagrammatic view of a high-pressure, high-temperature reactor utilizing a cantilever beam construction to measure the radial displacement force generated by a rotating test sample.
Figure 21:
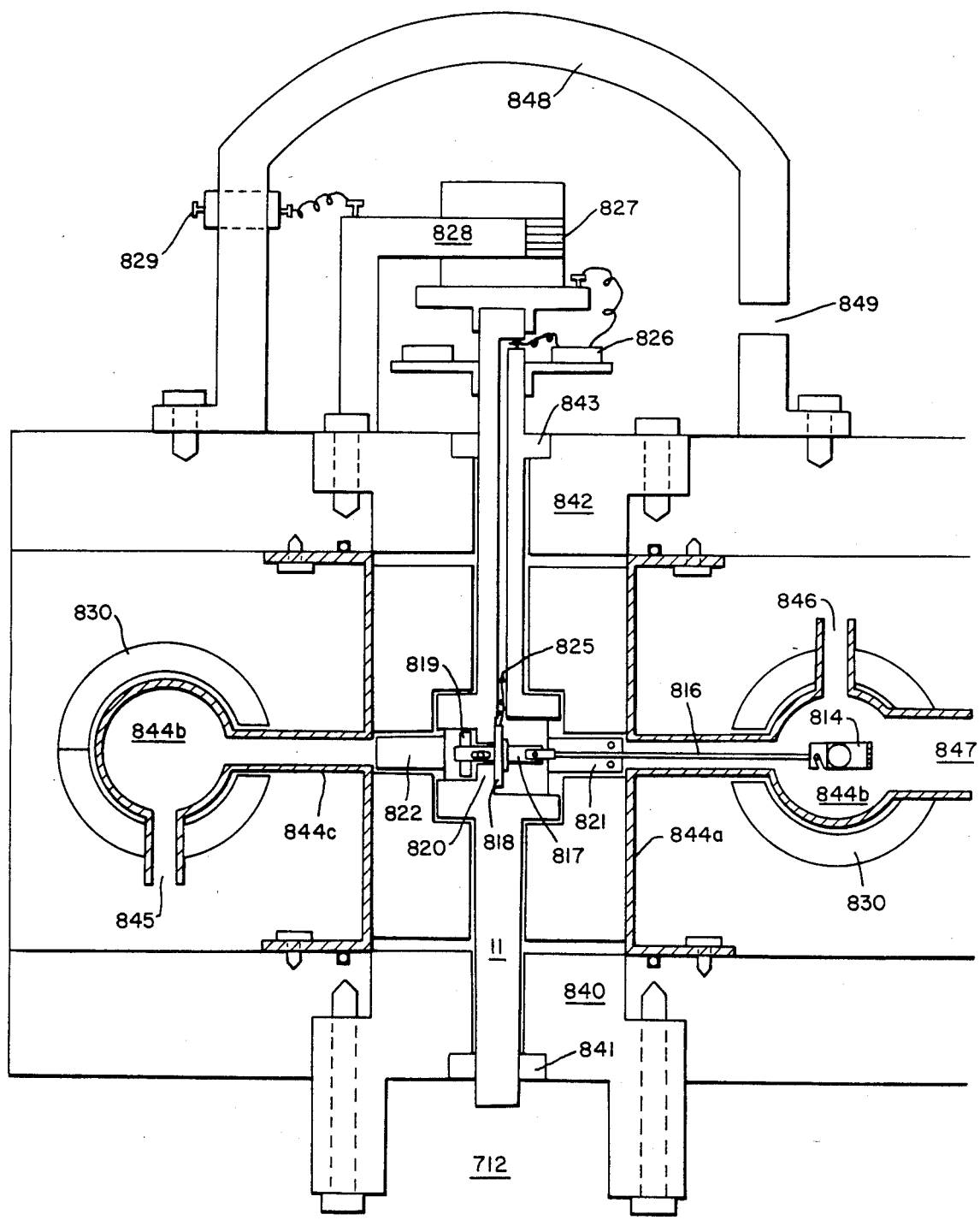
FIG. 21 is a partially cross-sectional and diagrammatic view of a high-temperature reactor with a quartz or glass reactor chamber that utilizes a load cell and a radial displacement force arm to measure a change in mass.
Figure 22:
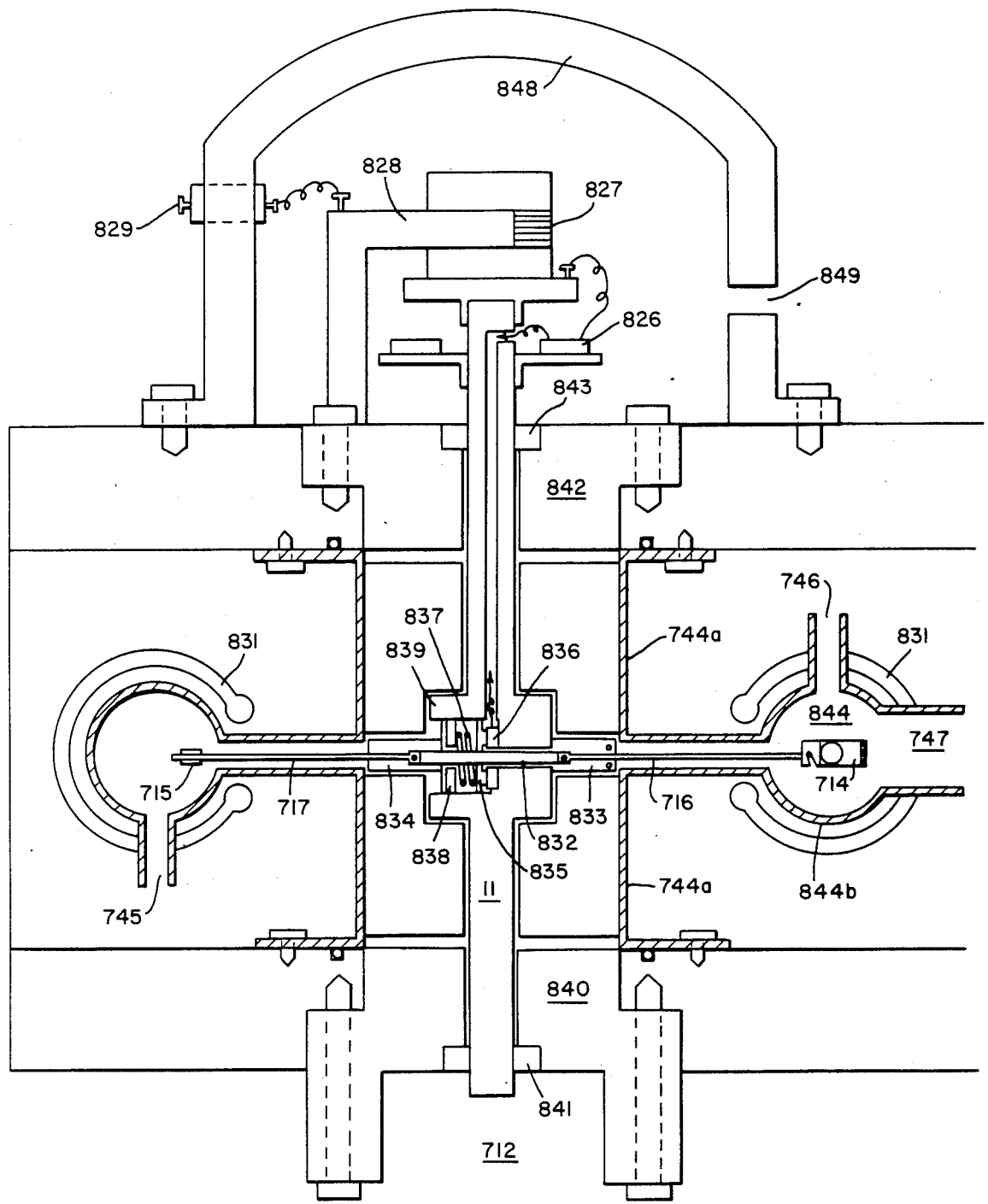
FIG. 22 is a partially cross-sectional and diagrammatic view of a high temperature reactor with a quartz or glass reactor chamber with a radial displacement force analyzer, using both a standard reference weight and a null force generator.

FIGS. 20, 21 and 22 illustrate the radial displacement and radial displacement force modes of operation. As illustrated in FIG. 20, the rotor arms 716 and 717 extend outwardly from the rotating shaft at 90 degrees from the shaft. In these embodiments, there is no second axis of rotation, and the displacement force is generated along a radial axis that is perpendicular to the axis of shaft 11.

As illustrated in FIG. 20, a radial displacement apparatus is illustrated in a high pressure, high temperature fluid reactor. A base housing 700 defines a support base for the reactor, the lower half of the reaction chamber 701, and provides a recess for bearing member 702 which supports the lower most portion of shaft 11. Base member 700 also defines a cavity 712 for receiving a drive motor (not shown) to drive shaft 11. The second half of the reactor, 703, defines the upper portion of reactor cavity 701, and instrumentation chamber 704 and provides a recess for bearing 705 which supports the upper portion of shaft 11. As illustrated in FIG. 20, shaft 11 has an enlarged portion 11a which receives a cantilever beam support 706. Support arms 716 and 715 are cantilevered from the vertical support member 706a. Support member 706 is precisely centered in shaft 11a by means of adjustment screws 707 and 708. The vertical support member 706 has an elongated vertical member 706a which is coaxially aligned along the axis of rotation of shaft 11. A strain gauge 709 is mounted on the elongated shaft 706a to provide an indication of deflection arising from radial displacement of member 706a by means of the radial displacement force exerted thereon by rotating test sample 714 and reference weight 715. Strain gauge 709 is connected to preamplifier 710 by means of a cable 711 which passes through shaft 11. A second cable 712 connects the preamplifier 710 to a slip ring 713a mounted on the upper end of shaft 11. The slip ring 713a and slip ring commutator 713b provide a rotorary to stationary connection for the output of strain gauge 709. The stationary commutator is then connected to an output terminal 760 for interconnection with the remainder of the apparatus circuitry. The strain gauge 709 may contain a wheatstone bridge circuit, which is suitable for static strain measurement, and a ballast circuit which is suitable for dynamic strain measurements. Additional strain-gauge circuitry may also be mounted on the rotating shaft 11, or in the cabinet housing 761 mounted above rotating shaft 11. The instrumentation chamber 704 is accessed by means of hatch 762 and is cooled by means of a gas inlet port 718. The strain gauge and rotating shaft 11 are cooled by air or gas which circulate from inlet ports 719 and 719a to exhaust ports 720a, and 720b which provides for a high speed purging of the high temperature gases present in the reaction chamber 701. The reaction gases are admitted to the reaction chamber 701 by means of inlet port 721 and exhausted by means of exhaust port 722. Close tolerances that are possible with the radial displacement mode permit a centrifugally outward sweep of gas through the annular passageway 723. A thermocouple well 724 provides a means for monitoring the temperature of the reaction chamber. An electrical heating means 725 and 726 provide means for heating the interior of the reaction chamber 701 to temperatures as high as 2500 degrees. A solids loading port 727 is provided in the upper portion of the support member 703 and is capped by means of plate 728.

As illustrated in FIG. 20, when the device is at rest, the solids container 714, which may assume the configuration of the container illustrated in FIG. 10, is loaded through access port 727. The device is then rotated to provide for the adjustment of reference weight 715 to balance the cantilever beam. As the device is rotated, the sample receiving means 714 is displaced outwardly as illustrated in FIG. 20, as the device achieves a preselected initial operating speed. After the desired rotational speed has been reached, the reaction study is begun by heating the autoclave chamber 701 by means of electrical resistance heating means 725 and 726, and then admitting the desired reaction gas through port 721. As the sample in the sample receiving means 714 undergoes a change in mass, the net change is reflected in a dynamic unbalance of the mass on rotor arms 716 and 717. This unbalance is then measured by strain gauge 709 and a ballast circuit to provide a derivative value of the change in mass, as amplified by the centrifugal force generated by the thermocentrifugometric analyzer.

In the apparatus illustrated in FIG. 21, the support members 840 and 842 define recesses for bearings 841 and 843 which support shaft 11 for rotation. In between support members 840, 842 is a glass or quartz reactor tube 844 which defines an annular cylinder 844a and a toroidal reaction chamber 844b interconnected with the cylindrical member 844a by means of an annular chamber 844c. The quartz reaction chamber defines a gas inlet port 845 and a gas exhaust port 846 for admission of preselected reaction gases. A solids loading port 847 is also defined at one portion of the reactor tube. In operation, ports 845 and 846 are connected to a supply and exhaust of the desired reaction gas, and port 847 is capped during the reaction period. An instrumentation chamber 848 also defines an inlet port 849 for the admission of a cooling fluid. The configuration of shaft 11 is somewhat different than that previously described with respect to FIG. 20. The solid sample holder 814 is suspended from support arm 816 which is pivotably mounted to a support member 817 mounted along a 90 degree radial axis with respect to the axis of rotation of shaft 11. Member 817 is mounted on a load cell 818 which is secured to shaft 11 by nut 819 on the other side of support web 820. While member 817 does not visually reciprocate, it does reciprocate to the extent necessary to transmit the displacement force generated by the rotating test sample and test sample receiving means 814 to load cell 818 as the sample undergoes a change in mass. A rotating vane and radiation shield 821 is mounted on the rotating shaft and protect load cell 818 from reaction chamber 844b. Diametrically opposed to rotating vane and shield 821 is a second vane 822. This enables the shaft to be dynamically balanced.

Load cell 818 may be of several different types. The reciprocal displacement is extremely small. For example, strain gauge load cells involve only a fraction of a thousandth of an inch of reciprocal movement. The linear variable differential transformer load cells involve larger displacements and may require additional force compensation. A typical load cell for use in a device as illustrated in FIG. 21 is the ELF-1000 series flat line load cell manufactured by Entran Devices Inc., 10 Washington Avenue, Fairfield, N.J. 07006. These load cells have a self contained wheatstone bridge, whose output is transmitted along cable 825 to compensation module and preamplifier circuit 826. The output of the preamplifier 826 is fed to a rotating commutator rings 827 and thence to the stationary slip ring 828 for connection to the outside of the instrumentation chamber as indicated by terminal 829. The quartz reaction chamber 844b is heated by means of radiant heaters 830 which surround the torroidal portion of the quartz reaction chamber.

The apparatus illustrated in FIG. 22 is similar in many respects to the apparatus illustrated in FIG. 21. A quartz reaction chamber is suspended between a lower support or base member 840 and an upper support or base member 842. However, the toroidal portion of the quartz reaction chamber is surrounded by an induction coil 831 for inductively heating the sample contained in the rotating sample receiving means 714. With the exception of the load cell and reciprocating apparatus mounted in rotating shaft 11, the remainder of the device is identical to the apparatus illustrated and described with repect to FIG. 21. A reciprocating shaft member 832 is mounted for reciprocation in shaft 11 and has attached thereto support arms 716 and 717. Support arms 716 supports the solid sample receiving means 714 and rotating arms 717 supports the reference weight 715. The load cell and shaft 11 are protected from the intense heat and/or radiation present in the annular chamber 844 by means of the baffles and radiation shields 833 and 834. These create a purging outward centrifugal flow of gas from the cavity surrounding shaft 11 to the angular reaction chamber 844. Attached to piston 832 is a reciprocating disc 835 which is biased into engagement with a load cell 836 by means of spring means 837. The spring means 837 is retained in position against the reciprocating disc 835 by means of a threaded nut 838 which is externally threaded to engage the threads 839 defined on the interior walls of the recess of shaft 11.

In operation, the sample receiving means 714 is loaded through the solids loading port 747, and the device is dynamically balanced while rotating by means of weight 715. After the device is dynamically balanced, the initial rotational speed of the device is selected, and a variable speed DC motor mounted in recess 712, is used to drive shaft 11 to its preselected operating speed. The load cell 836 is compressed by means of the radial force generated by the sample and sample receiving means 714, and transmits the output of its wheatstone bridge to preamplifier 826. The output of the preamplifier is transmitted by means of the commutator ring 827 to the output terminal 829. Spring means 837 provides a positive loading for load cell 836, even if the sample received in the sample receiving means 714 is reduced to zero mass.

Each of the principal embodiments previously illustrated with respect to FIGS. 1, 4, 7, 13, 14, 15, 16, 20, 21 and 22 disclose an angularly extending arm having a basket suspended therefrom for receiving a test sample to be measured. FIG. 10 describes an alternate embodiment of the sample holding means wherein the basket 13 is replaced with a unique solids container 111.

The test samples to be measured may come in a variety of sizes ranging from large particles to very fine powders. For big particles, a loosely woven basket such as that illustrated in FIG. 1 is quite satisfactory since the weave, in comparison to the size of the tested particles, allows the fluid or gas to pass freely between the solids. The basket configuration however is not satisfactory for very fine powders because even a small layer of such powders would force the fluid to deflect and pass around the container. In the example illustrated in FIG. 10, the fluid path 112 to be impinged upon the test sample to be analyzed is directed at the solids container 111 to enter the mouth 113 of the container. The solids container 111 has drilled therein a duct 114 illustrated by the dotted lines in FIG. 10. The duct terminates in a discharge screen 115 which is secured to the solids container 111 by welding or by means of plate 116 and a plurality of screws, one of which is illustrated on 117. The fluid flow through the duct 114 can be further increased by placing an air foil at the discharge end, or by making the diameter of the mouth 113 ($D_m$) somewhat larger than the diameter of the discharge exit 118 ($D_2$).

The unique solids container described in FIG. 10 provides gas-solid mass transfer rate as predicted by the Froessling equation:

$$Sh = 20 + 1.80 Sc^{\frac{1}{3}} Re^{\frac{1}{2}}$$

The effects of film mass and heat transfer resistances on the observed gas-solid reaction rate measurements are well known. For first order irreversable reactions, the observed reaction rate is given by:

$$R_A = \frac{P_{Ag}}{\frac{1}{k_g} + \frac{1}{k_s}}$$

In which $R_A$ is the rate of disappearance of gas A per unit surface area of solid, $P_{Ag}$ is the measurable and controllable bulk gas particle pressure of A, $k_g$ is the film mass transfer coefficient, and $k_s$ is the reaction rate constant measured on the surface of the reacting solid. In order for the observed reaction rate to represent the true reaction mass under both mass conditions, it is necessary that the mass transfer coefficient be much greater than the surface reaction rate constant, or $k_g > k_s$ and that the surface temperature of the solid be identical to the bulk gas temperature. This requires that the gas and solid be contacted at sufficiently high velocities. In the present invention, a gas velocity of 40 meters per second may be achieved at 4000 rpm. This high sweep gas rate may be achieved in a unique high temperature quartz reaction chamber at temperatures in excess of 1500 degrees. Even higher sweep rates can be used with operating speeds as high as 10,000 rpm.

Figure 12:
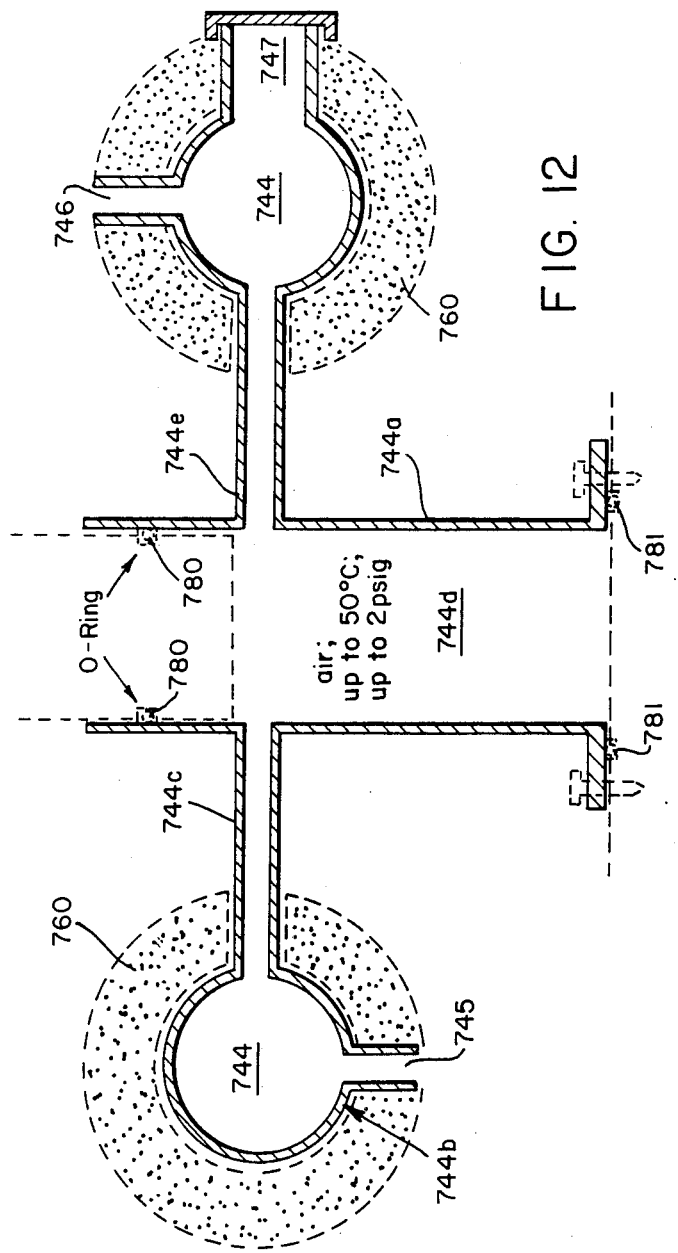
FIG. 12 is a cross-sectioned and diagrammatic view of a quartz or glass reactor that may be used with any embodiment of the present invention.

FIG. 12 describes the cross section of a unique quartz reaction chamber for use in the thermocentrifugometric analyzer. As illustrated in FIG. 12, the reaction chamber includes a central cylindrical portion 744a, a toroidal member 744b which surrounds the cylinder, and an annular chamber member 744c. The toroidal member 744b defines a reaction chamber 744 for high temperature reaction studies. The device is particularly adapted to radiant heat studies wherein a radiant heater 760 is placed around the quartz tube 744b. An inlet port 745 is formed on one side of the device, and an exhaust port 746 is formed on the opposite side of the toroidal cavity 744. Inlet 745 and exhaust 746 are used for admission and exhaust of the reaction gas introduced into chamber 744. A solids loading port 747 is formed on one side of the toroidal cavity 744. This solids loading port is normally capped with a cap 747a as illustrated in FIG. 12. Gas is normally introduced into the central cavity 744d to provide a purging and cooling gas flow for the rotating shaft and circuitry installed on rotating shaft 11. If desired, O-rings 780 and 781 may be used to seal the quartz reaction chamber. During operation, gas is normally introduced into cavity 744d at pressures up to 2 psi higher than that in chamber 744 to radially displace the gas flow towards the reaction chamber 744. In addition, the rotation of shaft 11 and of the rotor arms 716 and 717 will cause a radial outflow of the gas through the annular passageway defined at 744c.

Figure 9:
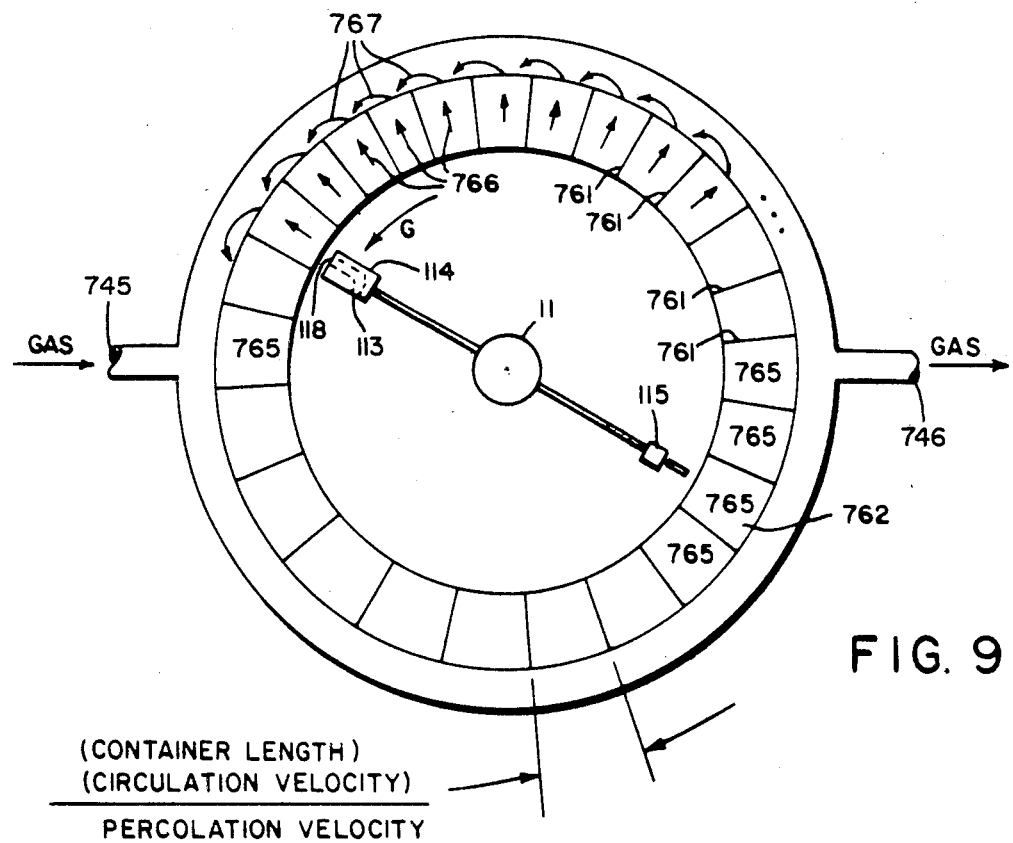
FIG. 9 is diagrammatic illustration of an annular chamber that may surround the rotational path of a test sample to limit the circumferential flow of a fluid induced by rotation of the sample.

An alternate reaction chamber is disclosed at FIG. 9. FIG. 9 illustrates diagrammatically, a means that may be installed in an autoclave chamber to assist in gas-solid reaction studies.

The rotation of shaft 11 and basket 114 may induce a whirling motion of the gaseous reaction media, however, a stationary gas is desireable. One means for inhibiting whirling motion and continuing the gas motion to a radial motion rather than a circumferential motion is disclosed in FIG. 9. The primary mechanism of gas mixing in the reactor is displacement mixing. It utilizes a percolating gas flow through the rotating container 114. When the device illustrated in FIG. 9 is used for the mixing, the calculations show that the displacement flow, occuring in the direction of rotation G, but without creating any significant gross whirling motion of gas, will amount to rpm×active displacement volume for each container summed over the containers 114 and 115, or 4000×0.02×2=1600 cm⁴/minute for the tested apparatus and container shown in FIG. 9 when rotating at 4000 rpm. Additional containers may be installed on the rotating shaft by means of extension arms to further enhance the gas mixing rate. When the angular momentum of the displacement gas discharged from the rotating container is mechanically dissipated by means of the appropriately spaced baffles 761, the gas flow pattern in the reaction chamber will be much like the cross recycle flow pattern illustrated by arrows 766 and 767.

The normal rotation of the solid sample receiving means 114 as illustrated in FIG. 9 causes a circumferential and centrifugal movement of the gas along the direction of arrow G illustrated in FIG. 9. By placing an annular baffle ring immediately outside the circumferential path of the sample receiving means 114, the gaseous fluid is directed outwardly rather than circumferentially. As was indicated in FIG. 10, the solid receiver 114 has an inlet opening 113 and an exhaust opening 118 the rotation of the solid receiver 114 forces the gas into port 113 and out of exhaust port 118. The series of radial baffles 761 are positioned around the axis of rotation of shaft 11. The distance between the baffles may be determined by the following formula:

$$\text{baffle distance} = \frac{\text{(container length)} \times \text{(circulation velocity)}}{\text{(percolation velocity)}}$$

The radial baffles 761 are secured by a pair of annular plates, one of which is illustrated as 762 in FIG. 9. The height of the baffles 761, and the spacing of the annular plates 762 and 763 (not shown) is determined by the size of the solids container 114. In operation, the reaction gas is admitted through port 745 and discharged through port 746.

Perfect mixing of the gas is essential in order to operate the thermocentrifugometric analyzer as an integral mixed flow reactor. This insures uniform bulk gas composition throughout the entire reactor gas space without using extensively large gas throughput rates. The gas mixing in the reactor is primarily dependent on the displacement flow of the gas produced by the rotating container 114, in the direction of the arrow G.

FIG. 13 discloses another alternate arrangement for measuring the angular displacement of rotor 13 in a thermocentrifugometric mass analyzer. As illustrated in FIG. 13, the rotating shaft 11 is powered by means of a variable speed drive motor 12 to rotate baskets 14 and 15 about a first axis of rotation A—A'. The shaft 11 is secured by a thrust bearing 135 and the autoclave chamber is sealed at 136 and 136a to prevent the escape of high temperature, high pressure gas. The gas may be admitted into the autoclave 40 by means of inlet 61 and exhausted through conduit 62 as has been previously described with respect to FIG. 2. A cooling chamber 135a is provided to insulate the autoclave from the driving and support mechanisms.

In the device illustrated in FIG. 13, an optical readout means is provided wherein a light source or any other radiant energy source 137 is positioned directly above rotor 13 and projects a beam of radiant energy 138 downwardly along axis A—A' through a quartz lens 144. An optical reflector means 139 is formed in rotor 13 to substantially deflect the beam of light or radiant energy from axis A—A' to a perpendicular axis indicated at 140. A quartz window 141 is provided in the wall of autoclave 40 with a series of photodiodes or other radiant energy responsive devices 142 arranged on the exterior of the autoclave chamber adjacent the quartz window. During operation of the device, the angular rotation of disc 13 causes a vertical displacement H—H' of the beam of radiant energy 140. As the beam or light ray sweeps past the quartz window 141, it energizes one of the photodiodes or other light sensitive devices 142 arranged on the exterior of the autoclave. The area energized is then converted into a measurement indicative of the angular displacement of rotor 13 by display device 143. Alternately, the value of the change in mass for the sample and container 14 may be calculated and displayed.

An alternate placement for light source 137 is indicated by dotted lines 137a in FIG. 13 wherein the light beam or beam of radiant energy is projected downwardly through a quartz lens 144a into the autoclave chamber 40. A portion of the support arm 16 designated at 145 is provided with a reflective device to reflect the light beam 138a through the quartz window 141 to strike the photodiode array at 142a. In this embodiment, an alternate compensating weight is added at 146 on the support arm 17. In each case, the device generates a single pulse of light on the photodiode array 142 for each revolution of shaft 11. The angular displacement of the beams 140 and 140a provide a derivative value of the change in mass in $M_S$ as the sample is subjected to preselected temperature and fluid variables.

Figure 15:
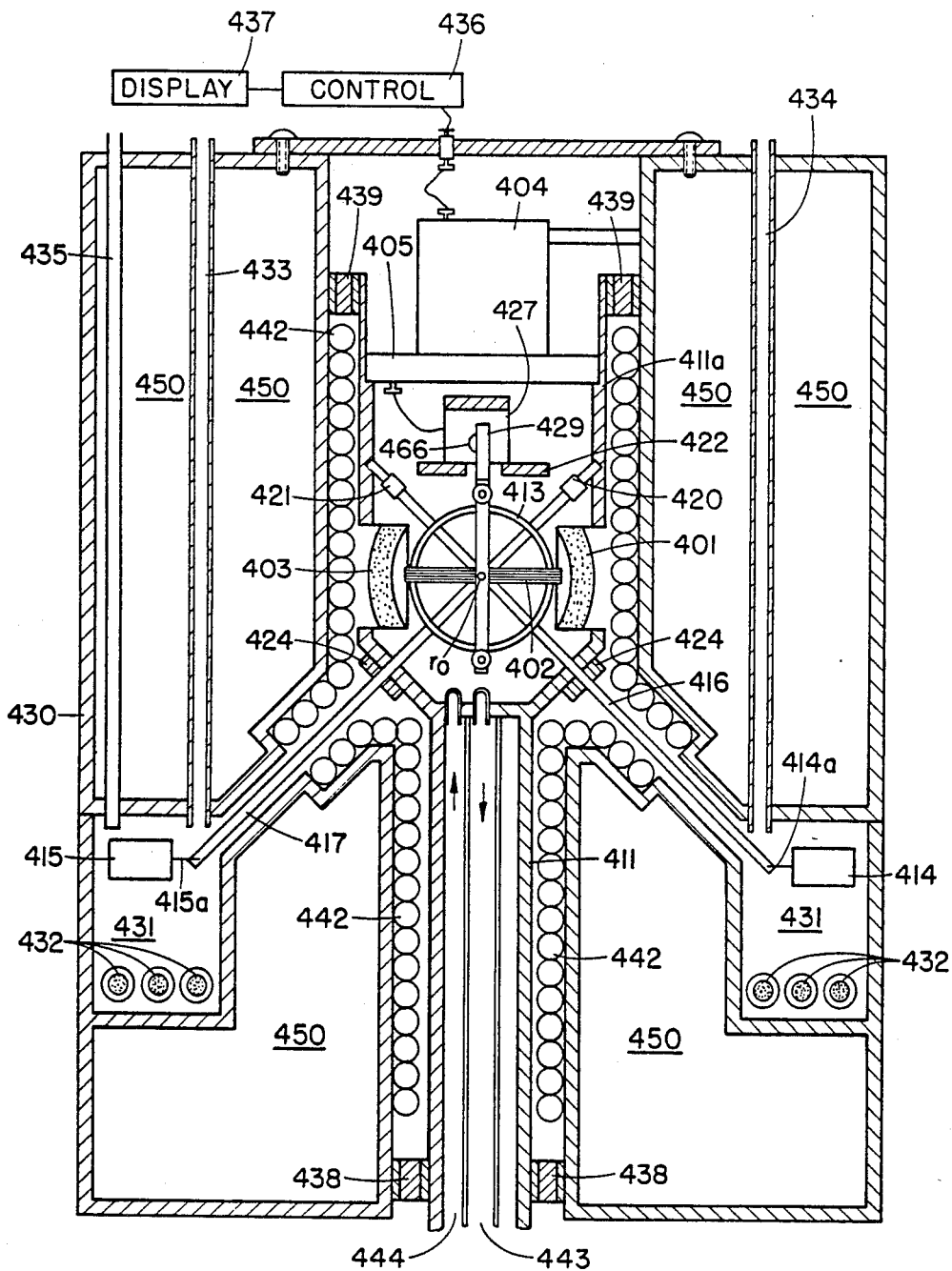
FIG. 15 is a cross-section view illustrating the use of the embodiment illustrated in FIG. 3 in an extremely high temperature autoclave.

FIGS. 15 and 16 illustrate the use of the embodiments previously described with respect to FIGS. 3 and 8 and a high temperature autoclave environment. Both devices are "null" type devices involving very little angular displacement of the rotors inasmuch as any angular displacement is immediately compensated for by a compensating restoring force.

As illustrated in FIG. 15, a high temperature autoclave 430 is constructed with an annular autoclave chamber 431 which is heated by means of electric heating coils 432. For extremely high temperature applications the container hangers 414a, 415a may be extended for increased thermal isolation of the gas chamber 431. In addition, if desired, the electrical heating means 432 may be replaced by an externally mounted radiation heating means with its thermal radiation focused along the circulation path of the container 414. The autoclave chamber is also supplied with a gas or fluid inlet conduit 433, and a gas or fluid outlet conduit 434. A thermocouple well 435 extends from above the cabinet 430 into the annular reaction chamber 431.

As was indicated previously with respect to FIG. 3, shaft 411 rotates rapidly with or without a reference weight $M_r$ in basket 415 and with a sample $M_S$ in basket 414. Static compensator weights 420 and 421 compensate for the rotor and provide rotor balance calibration weights. The rotor 413 rotates about $r_o$ upon a change in mass in $M_S$ carried by basket 414. This rotation is detected by means of photo-sensor 466 carried within transducer 427, as flag 429 moves from its center nulled position. As the photo-sensor 466 generates a control signal, the control signal is passed by means of rotating slip ring commutator 405 to the stationary slip ring commutator 404 to the control circuitry illustrated at 436. The control circuitry then energizes either coil 402 or 403, or both to generate a restoring force to return rotor 413 to its central nulled position wherein each of the arms 416 and 417 are equally aligned along the axis of rotation of shaft 411. Shaft 411 is journaled for rotation bearings 438–439 to provide for high speed rotation of the rotor arms 416 and 417. As was indicated previously with respect to FIG. 1, the speed of rotation may be several thousand rpm. In addition, the temperatures generated in the high temperature autoclave may be as high as 2,500 degrees. Cooling coils generally illustrated at 442 totally surround shaft 411 and 411a, and rotor 413 to insulate and cool the operating structure from the intense temperatures generated in the autoclave chamber 431. In addition, the reflective and insulated means 424 previously described with respect to FIG. 6, radiate the heat back towards the annular autoclave chamber 431. In addition to the coolant circulated through the coils 442, the shaft 411 may be cooled from the interior by means of coaxial conduits 443 and 444. In this embodiment, the annular conduit 444 provides a coolant inlet, while the center conduit 443 provides an outlet for the coolant.

The amount of current supplied to coil 402 and/or coil 403 to restore rotor 413 to a centered null position is then converted to a numerical display at 437 that may provide an indication of the change of weight in $M_s$ as it is reacted with the gaseous or fluid medium in the high temperature autoclave 431. The display for 437 may be an absolute or a functional value as desired.

The remainder of the interior within cabinet 430 is filled with insulation as indicated at 450.

The application of the "null" balance beam device to a high temperature autoclave environment is illustrated in FIG. 16. An autoclave cabinet 530 is used to house an annular high temperature autoclave chamber 531, and provides support bearings 538–539 for the rotating shaft 511. Rotating shaft also has support vanes 562 and 563 and an angularly displaceable arm 519 which rotates about pivot point 564 in the same manner as was described with respect to FIG. 7. The angular displacement of arm 519 caused by a change in $M_s$ placed in basket 514 is translated into vertical, reciprocal movement of reciprocating rod 520. The vertical force is translated by means of platter 524 to the balance beam 521 in the same manner as was previously described with respect to FIG. 7. The control apparatus for FIG. 16 is the same as was illustrated with respect to FIG. 8. A null balance is preferred for the high temperature autoclave, inasmuch as it is desired to isolate the high temperature autoclave chamber 531 from the instrumentation chamber 570 as much as possible. For extremely high temperature applications the container hanger 514a may be significantly extended for increased thermal isolation. As was previously indicated with respect to FIG. 8, the balance beam 521 exerts a counter force on reciprocating shaft 520 to maintain the arm 519 in a constant angular displacement. Forces acting on balance beam 521 may be generated by the null point gravimetric balance device 550, the compression type null device 552, a rotational motor 551, a linearly adjustable weight 544, or their combinations. The displacement of the balance beam 521 may be measured by the transducer 527 with respect to the metal or magnetic chip 529, or by the rotation of a rotational transducer 551 that measures the rotation of balance beam 521 about axis 526. As was previously indicated with respect to FIG. 8, electric, hydraulic or pneumatic devices may be used to generate the various forces on balance beam 521. Attached to vanes 562 and 563 are radiation shields 571 and 572 which may also be configured to provide maximum agitation of the gas or fluid in the high temperature autoclave chamber 531. High temperature fluid or gas is admitted through inlet port 533 and exited through exit port 534 during the reaction study. Or if desired, a given amount of reaction product may be introduced into the chamber 531, and the ports 533 and 534 sealed for the reaction. If desired, the rotating shaft 511 and the instrumentation chamber 570 may be insulated by cooling coils as was previously illustrated with respect to FIG. 15. The remainder of the chambers, however, are filled with insulation 550. If desired, the balance beam device illustrated in FIG. 16 may also be equipped with a conventional gravimetric scale 583 which is attached to balance beam 521 by means of cable 584 which passes through ports 580 and 581 and tubular member 582.

While the foregoing application has described a process and several distinctly separate mechanical devices for carrying out the process with substantial variations in the details of the specific embodiments it should be apparent that the teaching and disclosure of the present invention will suggest other embodiments and variations to those skilled in the art. Many mechanical, optical, electrical, and electromechanical transducer devices are present that could be readily adapted or modified for the present invention to provide indication of the angular rotation of the rotor means 13, or the angular force generated by the rotor means in the null motor apparatus or the beam balance apparatus, or the radial displacement or the radial displacement force in the radial displacement apparatus. One specific set of calculations has been included for test apparatus constructed and used in the determination of the change in mass of a test specimen subjected to elevated temperatures. The inclusion of the formulas as herein is not intended in any way to claim or restrict the use of the mathematical formula to applicant's invention, but is intended to teach those skilled in the art how to use applicant's invention to design centrifugometric mass analyzers capable of handling a variety of solid sizes in a variety of ambient operating conditions.

I claim:

1. A method for measuring a change in mass of a test sample when the sample is subjected to at least one selected temperature and fluid, said process comprising:
   (a) rotating a test sample about an axis to subject the sample to centrifugal force;
   (b) subjecting the test sample to at least one selected temperature and fluid to effect a change in mass of the test sample;
   (c) measuring a displacement force generated during the rotation of the test sample to determine a change in mass during an interval of time;
   whereby any change in mass in the test sample may be measured by a derivative value of the displacement forces generated at the beginning and end of said time interval.

2. A method for measuring a change in mass of a test sample as claimed in claim 1, wherein the displacement force generated by the rotating test sample is measured to obtain a derivative value of the mass of the sample.

3. A method for measuring a change in mass of a test sample as claimed in claim 1 wherein the speed of rotation is varied to balance the displacement force generated by the test sample against a known reactive force.

4. A method of measuring a change in mass of a test sample as claimed in claim 3 which further includes the step of suspending the test sample from a rotatable means, said means having a second axis of rotation perpendicular to the axis of rotation in step (a), and measuring a displacement about the second axis of rotation.

5. A method for measuring a change in mass of a test sample as claimed in 1 or 2 or 3 or 4 which further includes the step of generating at least one reactive force to balance the displacement force generated by the rotating test sample, and then measuring the reactive force.

6. A method for measuring a change in mass of a test material when the test material is subjected to at least one selected temperature and fluid, said process comprising:
   (a) rotating the test material about an axis to subject the test material to centrifugal force;
   (b) subjecting the test material to a selected temperature and fluid to effect a change in mass of the test material;
   (c) measuring a displacement of the sample during the rotation of the test sample to determine a change in mass during an interval of time;
   whereby any change in mass in the test sample may be measured by a derivative value of the displacement at the beginning and end of said time interval.

7. A method for measuring a change in mass of a test sample as claimed in claim 6 wherein the displacement generated by the rotating test sample is measured to obtain a derivative value of the mass of the sample.

8. A method for measuring a change in mass of a test material when said test material is subjected to at least one selected temperature and fluid, said process comprising:
   (a) balancing a test material with one or more known reactive force(s), said test material being placed in a rotatable test material receiving means,
   (b) rotating said test material receiving means about an axis to subject said test material to centrifugal force,
   (c) subjecting the test material to at least one selected temperature in fluid to effect a change in mass of said test material,
   (d) measuring the change in mass of said test material.

9. A method for measuring a change in mass of a test material as claimed in claim 8, wherein the test material is placed in a displaceable and rotatable test material receiving means, and the displacement is measured to determine the change in mass.

10. A method for measuring a change in mass of a test material is claimed in claim 8, wherein the speed of rotation is varied.

11. A method for measuring a change in mass of a test material as claimed in claim 8 wherein the speed of rotation is varied to balance the change in mass of the test material.

12. A method for measuring a change in mass of a test material as claimed in claim 8, wherein the speed of rotation and one or more reactive forces are varied to continuously balance the test material.

13. A method for measuring the change in mass of a test sample as claimed in claim 1 or 2 or 3 or 4 or 6 or 7 or 8 or 9 or 10 or 11 or 12 which further includes the step of rotating the sample in a sample receiving means rotatable between 200 rpm and 5000 rpm.

14. A method of measuring the change in mass of a test sample as claimed in claim 13, which further includes the step of directing a high velocity gaseous fluid against the test sample as it is rotated.

15. A method of measuring the change in mass of a test sample as claimed in claim 1 or 2 or 3 or 4 or 6 or 7 or 8 or 9 or 10 or 11 or 12 which further includes the steps of:
   (a) rotating the sample at a speed of at least 200 rpm;
   (b) elevating the temperature of the ambient atmosphere surrounding the sample to a preselected temperature.

16. A method of measuring the change in mass of a test sample as claimed in claim 15 which further includes the step of surrounding the sample with a preselected fluid.

17. A method of measuring the mass of a test sample as claimed in claim 16, which further includes the step of suspending the sample, which is solid, for rotation and sublimating it by a reaction with a preselected fluid.

18. A method for measuring a change in mass of a test sample as claimed in claims 1 or 2 or 3 or 4 or 7 or 8 wherein the change in mass is continuously measured.

19. A method for measuring a change in mass of a test sample as claimed in claim 1 or 2 or 3 or 4 or 7 or 8 wherein the change in mass is adapted to be measured by a differentiated value of displacement forces at the beginning and end of at least one finite interval of time.

20. A method for measuring a change in mass of a test sample as claimed in claim 1 or 2 or 3 or 4 or 8 which further includes the step of varying at least one adjustable force element to balance a change in displacement force generated by the test sample as it undergoes a change in mass.

21. A method for measuring a change in mass of a test sample as claimed in claim 20, which further includes the step of simultaneously varying the speed of rotation and at least one adjustable force element to balance the changing displacement force generated by the test sample.

22. A method for measuring a change in mass of a test sample as claimed in claim 1 or 4 or 6 or 7 or 8 which further includes the steps of:
   (a) placing the test sample in a displaceable sample receiving means;
   (b) balancing the test sample receiving means with a known reactive force before said sample is rotated.

23. A method for measuring a change in mass of a test sample as claimed in claim 22 wherein the known reactive force is generated by a reference weight before the test sample is rotated.

24. A method for measuring a change in mass of a test sample as claimed in claim 22 which further includes the step of generating one or more compensating forces to compensate for one or more rotating elements.

25. A method for measuring a change in mass of a test sample as claimed in claim 1 or 2 or 3 or 6 or 7 or 8 which further includes the step of measuring the displacement force generated with a transducer means positioned between the test sample and the axis of rotation.

26. A method for measuring a change in mass of a test sample as claimed in claims 1 or 2 or 3 or 4 or 8 which further includes the step of generating a reactive force to balance the displacement force generated with a variable beam balance.

27. A thermocentrifugometric analyzer for measuring the mass change of a test material subjected to at least one selected temperature and fluid, said analyzer comprising:

(a) a rotating shaft and means for rotating said shaft around a first axis of rotation;
(b) a test material holding means extending outwardly from said shaft to hold a test material while it is rotated about said axis of rotation;
(c) an enclosure means for subjecting the test material to at least one preselected temperature and fluid to effect a change of mass of said sample;
(d) a means for measuring a displacement force generated by said test material holding means when said test material is rotated about said axis of rotation and is subjected to said selected temperature and fluid.

28. A thermocentrifugometric analyzer as claimed in claim 27, wherein said means for measuring the displacement force further comprises a means for generating a null force to balance a displacement force generated by the rotating sample, and means for measuring the magnitude of the null force generated.

29. A thermocentrifugometric analyzer as claimed in claim 27, wherein said analyzer further includes a means for measuring the displacement force generated by the test sample at selected points in time as it is rotated.

30. A thermocentrifugometric analyzer as claimed in claim 27, wherein said means for measuring the displacement force comprises a balance beam.

31. A thermocentrifugometric analyzer as claimed in claim 30, wherein said balance beam initially balances the test material and test material holding means while rotating, said analyzer also having a control means for maintaining a dynamic balance of said apparatus with a variable null force to offset a change in the displacement force generated by the rotating test material, whereby any change in mass, over time, will be measured as a derivative value of the magnitude of the null force generated.

32. A thermocentrifugometric analyzer as claimed in claim 31, wherein said analyzer further includes a means for varying the speed of rotation of said shaft to rebalance said test sample to a reference weight as said test material undergoes a change in mass.

33. A thermocentrifugometric analyzer as claimed in claim 27, wherein said analyzer further includes a means for varying the speed of rotation of said shaft and said test material.

34. A thermocentrigugometric analyzer as claimed in claims 33 wherein said test material holding means is pivotably mounted on said shaft to rotate about a second axis of rotation, said second axis of rotation being perpendicular to said first axis of rotation.

35. A thermocentrigugometric analyzer as claimed in claim 34, wherein said analyzer further includes a reference weight to balance said test material about said second axis of rotation before said shaft is rotated.

36. A thermocentrifugometric analyzer as claimed in claim 27, which further comprises:
   (a) a means for generating a null force to offset a change in displacement force generated by the rotating test material;
   (b) a means for varying the null force in response to a change in displacement force and a means for generating a null signal representative of the applied null force;
   (c) a means for varying the speed of rotation to vary the magnitude of the displacement force generated by the test material and a means for generating a signal representative of the speed of rotation;

(d) a means for measuring the mass of the test material as a value derived from the displacement force signal and the speed of rotation signal.

37. A thermocentrifugometric analyzer as claimed in claim 36, wherein said analyzer further includes a reference weight of known mass to effectively vary the range of mass measurement.

38. A thermocentrifugometric analyzer for measuring the mass change of a test material subjected to at least one selected temperature and fluid, said analyzer comprising:
    (a) a rotating shaft and means for rotating said shaft around a first axis of rotation;
    (b) a test material holding means extending outwardly from said shaft to hold a test material while it is rotated about said axis of rotation;
    (c) an enclosure means for subjecting the test material to at least one preselected temperature and fluid to effect a change in mass of said test material;
    (d) a means for measuring any displacement of said test material when said test material is rotated about said axis of rotation and subjected to said selected temperature and fluid.

39. A thermocentrifugometric analyzer as claimed in claim 38 wherein said analyzer further includes a means for varying the speed of rotation of said shaft and said test material.

40. A thermocentrifugometric analyzer as claimed in claim 27 or 28 or 30 or 33 or 34 or 38 or 39, wherein said analyzer further includes an annular chamber surrounding a rotational path defined by said test material, said annular chamber having a series of radial baffles therein for converting circumferential flow of said selected fluid into a series of radial flow patterns.

41. A thermocentrifugometric analyzer as claimed in claim 27 or 28 or 30 or 33 or 34 or 38 or 39, wherein said test material holding means further includes a solid sample holder for receiving said test material, said sample holder having a first inlet opening oriented in the defined direction of rotation, a second outlet opening oriented along a radial axis when said analyzer is rotating, and means for retaining a solid test sample adjacent said second outlet opening.

42. A thermocentrifugometric analyzer as claimed in claim 27 or 28 or 30 or 33 or 34 or 38 or 39, wherein said analyzer further includes an annular reaction chamber, an autoclave surrounding said reaction chamber, and means for introducing a preselected fliud into said reaction chamber.

43. A thermocentrifugometric analyzer as claimed in claim 42, wherein said annular reaction chamber is formed of a high temperature resistant material such as glass or quartz.

44. A thermocentrifugometric analyzer as claimed in claim 27 or 28 or 30 or 33 or 34 or 38 or 39, wherein said enclosure means for subjecting the test material to preselected temperature and fluid variables further comprises:
    (a) a means for admitting at least one preselected fluid;
    (b) a means for withdrawing the preselected fluid;
    (c) a heating means;
    (d) a means for measuring the temperature of the fluid at least at one point in the enclosure space;
    (e) a control means responsive to the temperature measuring means for raising or lowering the temperature in a predicted manner and maintaining the temperature at a desired value.

45. A thermocentrifugometric analyzer as claimed in claim 33 or 39, wherein the means for rotating said shaft at variable speeds is responsive to said means for measuring the displacement force;
    whereby the displacement force generated by the test sample is maintained at a constant value as the speed of rotation is varied.

46. A thermocentrifugometric analyzer as claimed in claim 27 or 28 or 29 or 33 or 38 or 39, wherein said test material holding means is connected to said shaft by an outwardly extending arm.

47. A thermocentrifugometric analyzer as claimed in claim 27 or 29 or 33 or 38 or 39, wherein said enclosure is comprised of an annular chamber surrounding a rotational path defined by said test material, an inner chamber surrounding the rotating shaft, and a middle disc like space connecting said inner chamber to said outer chamber.

48. A thermocentrifugometric analyzer as claimed in claim 27 or 28 or 33 or 38 or 39, wherein said analyzer further includes a reference weight to balance said test material before said shaft is rotated.

49. A thermocentrifugometric analyzer as claimed in claim 27 or 29 or 38 or 39, wherein said analyzer further includes a cantilever beam mounted on said rotating shaft, said cantilever being supported by a first beam having a center axis aligned along the axis of rotation of said shaft, with said cantilever beam supporting said test material holding means, said analyzer also including a strain gauge mounted on said first beam for measuring a linear displacement force generated by measuring forces transmitted to the first beam by said cantilever beam.

50. A thermocentrifugometric analyzer as claimed in claim 27 or 28 or 38 or 39, wherein said analyzer further includes a reference mass to be rotated and thereby offset the force generated by the mass of said test material holding means.

51. A thermocentrifugometric analyzer as claimed in claim 27 or 29 or 38, wherein said measuring means further comprises a load cell.

52. A thermocentrifugometric analyzer as claimed in claim 29 or or 38, wherein said analyzer further includes a reference weight mounted to generate an opposing linear displacement force to at least partially offset the displacement force of said rotating test material holding means that is generated during testing.

53. A thermocentrifugometric analyzer as claimed in claim 27 or or 38, wherein said analyzer further includes a strain gauge mounted on said rotating shaft for measuring displacement force transmitted by said holding means to said rotating shaft.

54. A thermocentrifugometric analyzer as claimed in claim 27 or 38, wherein said analyzer further includes a compensator means mounted on a support means to compensate for the rotating mass of said test material holding means.

55. A thermocentrifugometric mass analyzer for measuring the mass change of a test material subjected to selected temperature and fluid variables, said analyzer comprising:
    (a) a rotating shaft, and means for rotating said shaft at varying speeds about a first axis of rotation,
    (b) a test material holding means extending outwardly from said shaft to hold said test material while it is rotated about said first axis of rotation,
    (c) an enclosure means for surrounding the rotating test material and subjecting said test material to at least one preselected temperature and fluid to effect a change in mass of said test test sample,
(d) a balance beam for balancing at least one null force and the centrifugal force generated by said rotating test material,
(e) means for translating a centrifugal force generated by said rotating test material to a reciprocal force connected to said balance beam,
(f) means for measuring the change in mass of said test sample from a change in the null force necessary to balance said balance beam.

56. A thermocentrifugometric mass analyzer as claimed in claim 55 wherein said means for measuring calculates the initial mass and a change in mass from the speed of rotation and the sum of the null force(s) applied to said balance beam.

57. A thermocentrifugometric mass analyzer as claimed in claim 56 wherein said analyzer further includes means for applying at least one predetermined force and one variable force to said balance beam.

58. A thermocentrifugometric mass analyzer for measuring the mass change of a test material subjected to at least one selected temperature and fluid, said analyzer comprising:
(a) a rotating shaft, and means for rotating said shaft about a first axis of rotation,
(b) a test material holding means extending radially outwardly from said first axis of rotation to hold said test material while it is rotated about said first axis of rotation,
(c) enclosure means for surrounding the rotating test material and subjecting said test material to at least one selected temperature and fluid to effect the change in mass of said test sample,
(d) a transducer means mounted between said rotating test material and said axis of rotation to convert the centrifugal force generated by said rotating test material into an electrical signal,
(e) means for computing a change in mass from said electrical signal.

59. A thermocentrifugometric mass analyzer as claimed in claim 58 wherein said transducer is mounted on a rotating shaft.

60. A thermocentrifugometric mass analyzer as claimed in claim 58 wherein said transducer is a load cell mounted to measure the radial force generated by the test material and test material holding means as they are rotated.

61. A thermocentrifugometric mass analyzer as claimed in claim 58 wherein said test material holding means further comprises:
(a) a reciprocating arm which reciprocates along a radial axis from said axis of rotation,
(b) means for resiliently biasing said arm to a first predetermined position to thereby oppose radially outward reciprocation of said arm during rotation of said test material and test material holding means,
(c) said transducer means measuring the radial reciprocation of said arm.

62. A thermocentrifugometric mass analyzer as claimed in claim 59 or 60 or 61 which further includes a compensator means mounted on said rotating shaft to generate an opposing radial displacement force to thereby at least partially offset the displacement force generated by said rotating test material holding means.

63. A thermocentrifugometric mass analyzer as claimed in claim 59 or 60 or 61 which further includes means for varying the rotational speed of said rotating shaft in response to a change in mass of said test material.

64. A thermocentrifugometric mass analyzer for measuring the mass change of a test material subjected to at least one selected temperature and fluid, said analyzer comprising:
(a) first means for rotating a test sample to increase its apparent mass through centrifugal force, said means rotating about a first axis of rotation,
(b) a test material holding means mounted on said first means and spaced from said axis of rotation for supporting said test material during rotation,
(c) second means for subjecting said test sample to at least one selected temperature and fluid to effect a change in mass in said test material,
(d) third means for measuring the change in mass of said test material.

65. A thermocentrifugometric mass analyzer as claimed in claim 64 which further includes variable drive means for changing the rotational speed of the analyzer.

66. A thermocentrifugometric mass analyzer as claimed in claim 65 wherein said test material holding means further includes a null motor having a second axis of rotation transverse to said first axis, said null motor generating a variable reaction force to compensate for a mass change in said test material; said null motor providing an output signal for said third means for measuring the change in mass of the test material.

67. A thermocentrifugometric mass analyzer as claimed in claim 64 which further includes compensating means to balance the apparent mass of the test material holding means during rotation thereof.

68. A thermocentrifugometric mass analyzer as claimed in claim 64 wherein said means for measuring the change in mass includes a transducer for generating an electrical signal responsive to said change.

69. A thermocentrifugometric mass analyzer as claimed in claim 68 which further includes:
(a) variable drive means for changing the rotational speed of the analyzer,
(b) control means responsive to said electric signal to vary the rotational speed in response to a change in mass.

70. A thermocentrifugometric mass analyzer as claimed in claim 64, 65, 66, 67, 68 or 69 wherein said means for subjecting said test sample to at least one selected temperature and fluid includes an autoclave chamber for heating the test material during rotation.

71. A thermocentrifugometric mass analyzer for measuring the mass of a test material subjected to at least one selected temperature, said analyzer comprising:
(a) rotatable means for rotating said test material at a plurality of selected speeds about about a first axis to thereby subject the test material to centrifugal force and thereby increase its apparent mass,
(b) a test material support means, said support means mounted on said rotatable means and supporting said test material means for rotation about a second axis of rotation,
(c) null motor means for generating a counter rotational force to oppose rotation about an axis of rotation, said null motor means providing an electrical signal indicative of the counter rotational force applied to said test material support means,
(d) means for subjecting the test material to at least one preselected temperature, (e) means for measuring the mass of the test material, said means responsive to said selected speed and said electrical signal to derive said measurement.

72. A thermocentrifugometric mass analyzer as claimed in claim 71 which further includes compensating means mounted on said support means to balance rotational moments about said second axis prior to the loading of a test material.

73. A thermocentrifugometric mass analyzer as claimed in claim 71 wherein the speed of rotation about said first axis is varied in response to a change in mass.

74. A thermocentrifugometric mass analyzer as claimed in claim 71 or 72 or 73 which further includes an autoclave chamber for surrounding the rotational path of said test material, and elevating the temperature of the fluid surrounding said sample to at least one preselected temperature.

75. A thermocentrifugometric mass analyzer as claimed in claim 74 which further includes means for thermally separating the rotational path of said test sample and said null motor means.

* * * * *